US 6,565,614 B1

(12) United States Patent
Genet et al.

(10) Patent No.: US 6,565,614 B1
(45) Date of Patent: May 20, 2003

(54) CATIONIC OXIDATION BASES, THEIR USE FOR OXIDATION DYEING OF KERATIN FIBRES, DYEING COMPOSITIONS AND DYEING METHODS

(75) Inventors: Alain Genet, Aulay-sous-Bois (FR); Alain LaGrange, Coupvray (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/254,662

(22) PCT Filed: Jul. 13, 1998

(86) PCT No.: PCT/FR98/01534

§ 371 (c)(1),
(2), (4) Date: Jun. 7, 1999

(87) PCT Pub. No.: WO99/03819

PCT Pub. Date: Jan. 28, 1999

(30) Foreign Application Priority Data

Jul. 16, 1997 (FR) .............................. 97 09027

(51) Int. Cl.⁷ ................................. A61K 7/13
(52) U.S. Cl. ............. 8/406; 8/407; 8/410; 8/416; 8/426; 8/654; 566/287; 566/282; 566/421
(58) Field of Search ................... 8/406, 407, 410, 8/416, 426, 654, 421; 564/287, 282

(56) References Cited

U.S. PATENT DOCUMENTS

| | | | |
|---|---|---|---|
| 3,100,739 A | 8/1963 | Kaiser et al. ................. 8/426 |
| 3,442,895 A | 5/1969 | Bugaut et al. ............... 544/156 |
| 3,467,483 A | 9/1969 | Bugaut et al. ................ 8/426 |
| 3,528,972 A | 9/1970 | Kalopissis et al. .......... 544/156 |
| 3,622,629 A * | 11/1971 | Lugosy ....................... 564/287 |
| 3,996,282 A | 12/1976 | Jefferies et al. |
| 4,103,092 A | 7/1978 | Jefferies et al. |
| 4,206,144 A | 6/1980 | Jefferies et al. |
| 4,888,025 A * | 12/1989 | Bugaut et al. ................. 8/416 |
| 4,975,092 A | 12/1990 | Chan et al. .................... 8/408 |
| 5,135,543 A | 8/1992 | Chan et al. .................... 8/405 |
| 5,137,538 A | 8/1992 | Madrange et al. ............. 8/410 |
| 5,139,532 A | 8/1992 | Chan et al. .................... 8/405 |
| 5,344,464 A | 9/1994 | Madrange et al. ............. 8/410 |
| 5,514,188 A | 5/1996 | Cotteret et al. ................ 8/412 |
| 5,735,908 A | 4/1998 | Cotteret et al. ................ 8/410 |
| 5,735,910 A | 4/1998 | Lagrange et al. .............. 8/415 |

FOREIGN PATENT DOCUMENTS

| | | |
|---|---|---|
| BE | 616 439 | 10/1962 |
| DE | 1 135 589 | 8/1962 |
| DE | 1 292 784 | 4/1969 |
| EP | 0 360 644 | 3/1990 |
| EP | 0 544 400 | 6/1993 |
| EP | 0 634 164 | 1/1995 |
| EP | 0 673 641 | 9/1995 |
| EP | 0 673 926 | 9/1995 |
| EP | 0 728 463 | 8/1996 |
| FR | 1 391 675 | 12/1965 |
| FR | 2134460 * | 8/1972 |
| FR | 2 213 968 | 8/1974 |
| FR | 2 217 390 | 9/1974 |
| FR | 2 288 093 | 5/1976 |
| FR | 2 586 913 | 3/1987 |
| FR | 2 630 438 | 10/1989 |
| GB | 1 211 801 | 11/1970 |
| GB | 1 299 080 | 12/1972 |
| GB | 2 018 453 | 10/1979 |
| JP | 49-118721 | 11/1974 |
| WO | WO 95/01772 | 1/1995 |
| WO | WO 95/12585 | 5/1995 |
| WO | WO 95/15144 | 6/1995 |
| WO | WO 97/39727 | 10/1997 |

OTHER PUBLICATIONS

C. Tomaier, "Phenols Anilines: Bases Coupleurs a Azote Quaternaire Extra–Nucleaire", Bibliographie No. 307, Jun. 1996, pp. 2–28.

C. Tomaier, "Bis–Quaternaires en Cosmetique", Bibliographie No. 317, Feb. 1997, pp. 2–35.

L.K.J. Tong et al., "The Mechanism of Dye Formation in Color Photography. VII. Intermediate Bases in the Deamination of Quinonediimines", Journal of American Chemical Scoeity, vol. 82, No. 8, Apr. 1960, pp. 1988–1996.

English language Derwent Abstract of EP 0 728 463, Aug. 1996.

English language Derwent Abstract of FR 2 213 968, Sep. 1974.

English language Derwent Abstract of FR 2 217 390, Oct. 1974.

English language Derwent Abstract of FR 2 586 924, Mar. 1987.

English language Derwent Abstract of FR 2 630 438, Oct. 1989.

* cited by examiner

*Primary Examiner*—Margaret Einsmann
(74) *Attorney, Agent, or Firm*—Finnegan, Henderson, Farabow, Garrett & Dunner, L.L.P.

(57) ABSTRACT

The invention relates to novel monobenzene oxidation bases containing at least one cationic group Z bearing at least one quaternary ammonium unit which may or may not be cyclized, to their use for the oxidation dyeing of keratin fibers, to dye compositions containing then and to oxidation dyeing processes using them.

34 Claims, No Drawings

CATIONIC OXIDATION BASES, THEIR USE FOR OXIDATION DYEING OF KERATIN FIBRES, DYEING COMPOSITIONS AND DYEING METHODS

The invention relates to novel monobenzene oxidation bases containing at least one cationic group Z, Z being chosen from quaternized aliphatic chains and aliphatic chains containing at least one quaternized saturated ring, to their use for the oxidation dyeing of keratin fibres, to dye compositions containing them and to oxidation dyeing processes using them.

It is known practice to dye keratin fibres, and in particular human hair, with dye compositions containing oxidation dye precursors, in particular ortho- or para-phenylenediamines, ortho- or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may be indeed be differently sensitized (i.e. damaged) between its tip and its root.

It has already been proposed, in particular in U.S. Pat. No. 5,139,532, to use certain cationic para-phenylenediamine derivatives, i.e. more precisely, para-phenylenediamines in which one of the amino groups is monosubstituted with a quaternized aliphatic chain, for the oxidation dyeing of keratin fibres in strong shades which are redder than those usually obtained using standard para-phenylenediamines, i.e. compounds containing no cationic groups. However, the use of the para-phenylenediamines described in that prior patent does not make it possible to obtain a wide range of colours and, furthermore, the colorations obtained are not always entirely satisfactory from the point of view of their resistance with respect to the various forms of attack to which the hair may be subjected (action of light, perspiration, shampoo, etc.).

Now, the Applicant has just discovered, entirely surprisingly and unexpectedly, that certain novel monobenzene oxidation bases of formula (I) defined below, containing at least one cationic group Z, Z being chosen from quaternized aliphatic chains and aliphatic chains containing at least one quaternized saturated ring, are not only suitable for use as oxidation dye precursors, but also allow dye compositions to be obtained which lead to strong colorations covering a wide range of colours and having excellent properties of resistance to the various treatments to which keratin fibres may be subjected. Lastly, these compositions prove to be readily synthesizable.

These discoveries form the basis of the present invention.

A first subject of the invention is thus novel compounds of formula (I) below, and the addition salts thereof with an acid:

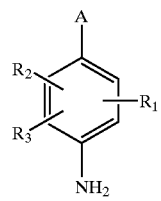

(I)

in which:

$R_1$, $R_2$ and $R_3$, which may be identical or different, represent a hydrogen atom; a halogen atom; a group Z; a ($C_1$–$C_6$)alkylcarbonyl radical; an amino($C_1$–$C_6$) alkylcarbonyl radical; an N-Z-amino($C_1$–$C_6$) alkylcarbonyl radical; an N-($C_1$–$C_6$)alkylamino ($C_1$–$C_6$)alkylcarbonyl radical; an N,N-di($C_1$–$C_6$) alkylamino($C_1$–$C_6$)alkylcarbonyl radical; an amino ($C_1$–$C_6$)alkylcarbonyl($C_1$–$C_6$)alkyl radical; an N-Z-amino($C_1$–$C_6$)alkylcarbonyl($C_1$–$C_6$)alkyl radical; an N-($C_1$–$C_6$)alkylamino($C_1$–$C_6$)alkylcarbonyl($C_1$–$C_6$) alkyl radical; an N,N-di($C_1$–$C_6$)alkylamino($C_1$–$C_6$) alkylcarbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N—Z-amino-sulphonyl radical; a $C_1$–$C_6$ N-alkylaminosulphonyl radical; an N,N-di($C_1$–$C_6$) alkylaminosulphonyl radical; a $C_1$–$C_6$ aminosulphonylalkyl radical; a $C_1$–$C_6$ N-Z-aminosulphonylalkyl radical; an N-($C_1$–$C_6$)alkylaminosulphonyl($C_1$–$C_6$)alkyl radical; an N,N-di($C_1$–$C_6$)alkylaminosulphonyl ($C_1$–$C_6$)alkyl radical; a carbamyl radical; an N-($C_1$–$C_6$) alkylcarbamyl radical; an N,N-di($C_1$–$C_6$) alkylcarbamyl radical; a carbamyl($C_1$–$C_6$)alkyl radical; an N-($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_1$–$C_6$ trifluoroalkyl radical; a cyano radical; a group $OR_6$ or $SR_6$; an amino group protected with a ($C_1$–$C_6$)alkylcarbonyl, ($C_1$–$C_6$) alkylcarboxyl, trifluoro($C_1$–$C_6$)alkylcarbonyl, amino ($C_1$–$C_6$)alkylcarbonyl, N-Z-amino($C_1$–$C_6$) alkylcarbonyl, N-($C_1$–$C_6$)alkylamino($C_1$–$C_6$) alkylcarbonyl, N,N-di($C_1$–$C_6$)alkylamino($C_1$–$C_6$) alkylcarbonyl, ($C_1$–$C_6$)alkylcarboxyl, carbamyl, N-($C_1$–$C_6$)alkylcarbamyl, N,N-di($C_1$–$C_6$) alkylcarbamyl, $C_1$–$C_6$ alkylsulphonyl, aminosulphonyl, N-Z-aminosulphonyl, $C_1$–$C_6$ N-alkylaminosulphonyl, N,N-di($C_1$–$C_6$) alkylaminosulphonyl, thiocarbamyl or formyl radical, or with a group Z; or a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, carbamyl, N-($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$) alkylcarboxyl and thiocarbamyl radicals, or with a group Z;

$R_6$ denotes a $C_1$–$C_6$ alkyl radical; a $C_1$–$C_6$ monohydroxyalkyl radical; a $C_2$–$C_6$ polyhydroxyalkyl radical; a group Z; a $(C_1$–$C_6)$alkoxy$(C_1$–$C_6)$alkyl radical; an aryl radical; a benzyl radical; a carboxy$(C_1$–$C_6)$alkyl radical; a $(C_1$–$C_6)$alkylcarboxy$(C_1$–$C_6)$alkyl radical; a cyano$(C_1$–$C_6)$alkyl radical; a carbamyl$(C_1$–$C_6)$alkyl radical; an N-$(C_1$–$C_6)$alkylcarbamyl$(C_1$–$C_6)$alkyl radical; an N,N-di$(C_1$–$C_6)$alkylcarbamyl$(C_1$–$C_6)$alkyl radical; a $C_1$–$C_6$ trifluoroalkyl radical; a $C_1$–$C_6$ aminosulphonylalkyl radical; a $C_1$–$C_6$ N-Z-aminosulphonylalkyl radical; an N-$(C_1$–$C_6)$alkylaminosulphonyl$(C_1$–$C_6)$alkyl radical; an N,N-di$(C_1$–$C_6)$alkylaminosulphonyl$(C_1$–$C_6)$alkyl radical; a $(C_1$–$C_6)$alkylsulphinyl$(C_1$–$C_6)$alkyl radical; a $(C_1$–$C_6)$alkylsulphonyl$(C_1$–$C_6)$alkyl radical; a $(C_1$–$C_6)$alkylcarbonyl$(C_1$–$C_6)$alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, $(C_1$–$C_6)$ alkylcarbonyl, formyl, trifluoro$(C_1$–$C_6)$alkylcarbonyl, $(C_1$–$C_6)$alkylcarboxyl, carbamyl, N-$(C_1$–$C_6)$ alkylcarbamyl, N,N-di$(C_1$–$C_6)$alkylcarbamyl, thiocarbamyl and $C_1$–$C_6$ alkylsulphonyl radicals, and the group Z;

A represents a group —$NR_4R_5$ or a hydroxyl radical;

$R_4$ and $R_5$, which may be identical or different, represent a hydrogen atom; a group Z; a $C_1$–$C_6$ alkyl radical; a $C_1$–$C_6$ monohydroxyalkyl radical; a $C_2$–$C_6$ polyhydroxyalkyl radical; a $(C_1$–$C_6)$alkoxy$(C_1$–$C_6)$alkyl radical; an aryl radical; a benzyl radical; a cyano$(C_1$–$C_6)$ alkyl radical; a carbamyl$(C_1$–$C_6)$alkyl radical; an N-$(C_1$–$C_6)$alkylcarbamyl$(C_1$–$C_6)$alkyl radical; an N,N-di$(C_1$–$C_6)$alkylcarbamyl$(C_1$–$C_6)$alkyl radical; a thiocarbamyl$(C_1$–$C_6)$alkyl radical; a $C_1$–$C_6$ trifluoroalkyl radical; a $C_1$–$C_6$ sulphoalkyl radical; a $(C_1$–$C_6)$ alkylcarboxy$(C_1$–$C_6)$alkyl radical; a $(C_1$–$C_6)$ alkylsulphinyl$(C_1$–$C_6)$alkyl radical; a $C_1$–$C_6$ aminosulphonylalkyl radical; a $C_1$–$C_6$ N-Z-aminosulphonylalkyl radical; an N-$(C_1$–$C_6)$ alkylaminosulphonyl$(C_1$–$C_6)$alkyl radical; an N,N-di$(C_1$–$C_6)$alkylaminosulphonyl$(C_1$–$C_6)$alkyl radical; a $(C_1$–$C_6)$alkylcarbonyl$(C_1$–$C_6)$alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, $(C_1$–$C_6)$ alkylcarbonyl, carbamyl, N-$(C_1$–$C_6)$alkylcarbamyl, N,N-di$(C_1$–$C_6)$alkylcarbamyl, $C_1$–$C_6$ alkylsulphonyl, formyl, trifluoro$(C_1$–$C_6)$alkylcarbonyl, $(C_1$–$C_6)$ alkylcarboxyl and thiocarbamyl radicals, or with a group Z;

Z represents a group of formula (II) below:

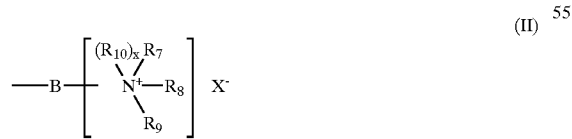

(II)

in which:

B is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1$–$C_6$ alkoxy radicals, and which can bear one or more ketone functions;

$R_7$, $R_8$ and $R_9$, which may be identical or different, represent a $C_1$–$C_6$ alkyl radical, a $C_1$–$C_6$ monohydroxyalkyl radical, a $C_2$–$C_6$ polyhydroxyalkyl radical, a $(C_1$–$C_6)$alkoxy$(C_1$–$C_6)$alkyl radical, a cyano$(C_1$–$C_6)$ alkyl radical, an aryl radical, a benzyl radical, a carbamyl$(C_1$–$C_6)$alkyl radical, a tri$(C_1$–$C_6)$alkylsilane $(C_1$–$C_6)$alkyl radical or a $C_1$–$C_6$ aminoalkyl radical in which the amine is protected with a $(C_1$–$C_6)$ alkylcarbonyl, carbamyl or $C_1$–$C_6$ alkylsulphonyl radical; two of the radicals $R_7$, $R_8$ and $R_9$ can together also form, with the nitrogen atom to which they are attached, a saturated 5- or 6-membered carbon ring or a ring containing one or more hetero atoms such as, for example, a pyrrolidine ring, a piperidine ring, a piperazine ring or a morpholine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano$(C_1$–$C_6)$alkyl radical, a $C_1$–$C_6$ alkoxy radical, a tri$(C_1$–$C_6)$alkylsilane$(C_1$–$C_6)$alkyl radical, an amido radical, an aldehydo radical, a carboxyl radical, a $(C_1$–$C_6)$alkylcarbonyl radical, a thio radical, a $C_1$–$C_6$ thioalkyl radical, a $C_1$–$C_6$ alkylthio radical, an amino radical or an amino radical protected with a $(C_1$–$C_6)$ alkylcarbonyl, carbamyl or $C_1$–$C_6$ alkylsulphonyl radical; one of the radicals $R_7$, $R_8$ and $R_9$ can also represent a second group Z which is identical to or different from the first group Z;

$X^-$ represents a monovalent or divalent anion and is preferably chosen from a halogen atom such as chlorine, bromine, fluorine or iodine, a hydroxide, a hydrogenosulphate or a $C_1$–$C_6$ alkyl sulphate such as, for example, a methyl sulphate or an ethyl sulphate;

$R_{10}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a $(C_1$–$C_6)$alkylcarbonyl, carbamyl or $C_1$–$C_6$ alkylsulphonyl radical; a carboxy$(C_1$–$C_6)$alkyl radical; a cyano$(C_1$–$C_6)$alkyl radical; a carbamyl $(C_1$–$C_6)$alkyl radical; a $C_1$–$C_6$ trifluoroalkyl radical; a tri$(C_1$–$C_6)$alkylsilane$(C_1$–$C_6)$alkyl radical; a $C_1$–$C_6$ sulphonamidoalkyl radical; a $(C_1$–$C_6)$alkylcarboxy $(C_1$–$C_6)$alkyl radical; a $(C_1$–$C_6)$alkylsulphinyl$(C_1$–$C_6)$ alkyl radical; a $(C_1$–$C_6)$alkylsulphonyl$(C_1$–$C_6)$alkyl radical; a $(C_1$–$C_6)$alkylketo$(C_1$–$C_6)$alkyl radical; an N-$(C_1$–$C_6)$alkylcarbamyl$(C_1$–$C_6)$alkyl radical; an N-$(C_1$–$C_6)$alkylsulphonamido$(C_1$–$C_6)$alkyl radical;

x is an integer equal to 0 or 1; with the following conditions:
when x=0, then the linker arm B is attached to the nitrogen atom bearing the radicals $R_7$ to $R_9$,
when x=1, then two of the radicals $R_7$ to $R_9$ form, together with the nitrogen atom to which they are attached, a saturated 5- or 6-membered ring as defined above, and the linker arm B is borne by a carbon atom of the said saturated ring;

it being understood:
that the number of groups Z is at least equal to 1;
that when A represents a group —$NR_4R_5$, in which $R_4$ or $R_5$ represents a group Z in which the linker arm B represents an alkyl chain containing a ketone function, then the said ketone function is not directly attached to the nitrogen atom of the group NR$_4$R$_5$;

and with the exclusion of 4-amino-2-fluoro-N-(trimethylammonioethyl)aniline iodide, 4-amino-2-trifluoromethyl-N-(trimethylammonioethyl)aniline iodide; 4-amino-2-cyano-N-(trimethylammonioethyl)aniline iodide; 2-(4-aminophenylamino)ethyltrimethylammonium iodide; 4-amino-3-methyl-N-ethyl-N-(trimethylammonioethyl)aniline chloride, and the addition salts thereof with an acid.

As mentioned above, the colorations obtained with the oxidation dye composition in accordance with the invention are strong and cover a wide range of colours. They moreover have excellent properties of resistance to the action of various external agents (light, bad weather, washing, permanent-waving, perspiration, friction).

In formula (I) above, the alkyl and alkoxy radicals can be linear or branched.

Among the compounds of formula (I) above, mention may be made in particular of:

[2-(2,5-diaminophenoxy)ethyl]diethylmethylammonium chloride monohydrate;
N,N-bis(trimethylammoniopropyl)-4-aminoaniline dichloride;
[4-(4-aminophenylamino)pentyl]diethylmethylammonium chloride;
[4-(4-aminophenylamino)pentyl]diethyl-(2-hydroxyethyl) ammonium chloride;
[2-(4-aminophenylamino)ethyl]diethylmethylammonium chloride;
{2-[(4-aminophenyl)methylamino]ethyl}trimethylammonium chloride;
[3-(4-aminophenylamino)propyl]trimethylammonium chloride;
[2-(4-aminophenylamino)propyl]trimethylammonium chloride;
[4-(4-amino-2-methylphenylamino)pentyl]diethylmethylammonium chloride;
[4-(4-amino-3-methylphenylamino)pentyl]diethylmethylammonium chloride;
1-{[5-amino-2-(2-hydroxyethylamino)phenylcarbamoyl]methyl}-1,4-dimethyl-1-piperazinium chloride; and the addition salts thereof with an acid.

Among these compounds of formula (I), the ones more particularly preferred are:

[2-(2,5-diaminophenoxy)ethyl]diethylmethylammonium chloride monohydrate;
N,N-bis(trimethylammoniopropyl)-4-aminoaniline chloride;
[4-(4-aminophenylamino)pentyl]diethylmethylammonium chloride;
[2-(4-aminophenylamino)ethyl]diethylmethylammonium chloride;
{2-[(4-aminophenyl)methylamino]ethyl}trimethylammonium chloride;
[3-(4-aminophenylamino)propyl]trimethylammonium chloride;
[4-(4-aminophenylamino)pentyl]diethyl-(2-hydroxyethyl) ammonium chloride;
and the addition salts thereof with an acid.

The compounds of formula (I) in accordance with the invention can be readily obtained according to methods that are well known in the state of the art:

either by reduction of the corresponding cationic nitro compounds (cationic para-nitroanilines or cationic para-nitrophenols), or by reduction of the corresponding cationic nitroso compounds (obtained, for example, by nitrosation of a tertiary aniline or of a corresponding phenol), or by reduction of the corresponding cationic azo compounds (reductive cleavage).

This reduction step (production of a primary aromatic amine) which gives the synthesized compound its nature as an oxidizable compound (oxidation base), which may or may not be followed by a salification, is generally, for convenience, the final step of the synthesis.

This reduction can take place earlier in the sequence of reactions leading to the preparation of the compounds of formula (I), and according to well-known processes it is then necessary to "protect" the primary amine created (for example by an acetylation, benzenesulphonation, etc. step), then carry out the desired substitution(s) or modification(s) (including quaternization) and end by "deprotecting" (generally in acidic medium) the amine function.

Similarly, the phenolic function can be protected according to well-known processes with a benzyl radical ("deprotection" by catalytic reduction) or with an acetyl or mesyl radical ("deprotection" in acidic medium).

When the synthesis is complete, the compounds of formula (I) in accordance with the invention can, if necessary, be recovered by methods which are well known in the state of the art, such as crystallization or distillation.

Another subject of the invention is the use of the compounds of formula (I) in accordance with the invention as oxidation bases for the oxidation dyeing of keratin fibres, and in of particular human keratin fibres such as the hair.

The invention also relates to a composition for the oxidation dyeing of keratin fibres, and in particular of human keratin fibres such as the hair, characterized in that it comprises, as an oxidation base, in a medium which is suitable for dyeing, at least one compound of formula (I) in accordance with the invention.

The compound(s) of formula (I) in accordance with the invention preferably represent(s) from 0.0005 to 12% by weight approximately relative to the total weight of the dye composition, and even more preferably from 0.005 to 6% by weight approximately relative to this weight.

The medium which is suitable for dyeing (or the support) generally consists of water or a mixture of water and at least one organic solvent to dissolve the compounds which would not be sufficiently soluble in water. As organic solvent, mention may be made, for example, of $C_1$-$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (III) below:

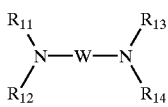 (III)

in which W is a propylene residue optionally substituted with a hydroxyl group or a $C_1$–$C_6$ alkyl radical; $R_{11}$, $R_{12}$, $R_{13}$ and $R_{14}$, which may be identical or different, represent a hydrogen atom, a $C_1$–$C_6$ alkyl radical or a $C_1$–$C_6$ hydroxyalkyl radical.

The dye composition in accordance with the invention can also contain, in addition to the dyes defined above, at least one additional oxidation base which can be chosen from the oxidation bases conventionally used in oxidation dyeing and among which mention may be made in particular of para-phenylenediamines other than the compounds of formula (I) in accordance with the invention, bis(phenyl)alkylenediamines, para-aminophenols other than the compounds of formula (I) in accordance with the invention, ortho-aminophenols and heterocyclic bases.

Among the para-phenylenediamines which can be mentioned more particularly, for example, are para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)para-phenylenediamine, N,N-bis(β-hydroxyethyl)-para-phenylenediamine, 4-amino-N-(β-methoxyethyl)aniline and the para-phenylenediamines described in French patent application FR 2,630,438, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

When they are used, these additional oxidation bases preferably represent from 0.0005 to 12% by weight approximately relative to the total weight of the dye composition, and even more preferably from 0.005 to 6% by weight approximately relative to this weight.

The oxidation dye compositions in accordance with the invention can also contain at least one coupler and/or at least one direct dye, in particular in order to modify the shades or to enrich them with glints.

The couplers which can be used in the oxidation dye compositions in accordance with the invention can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 6-hydroxybenzomorpholine, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the dye composition and even more preferably from 0.005 to 5% by weight approximately relative to this weight.

In general, the addition salts with an acid which can be used in the context of the dye compositions of the invention (compounds of formula (I), additional oxidation bases and couplers) are chosen in particular from the hydrochlorides, hydrobromides, sulphates, citrates, succinates, tartrates, lactates and acetates.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially in a separate manner.

According to a preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2,586,913 in the name of the Applicant.

The examples which follow are intended to illustrate the invention without, however, limiting its scope.

PREPARATION EXAMPLES

Preparation Example 1

Synthesis of [2-(2,5-diaminophenoxy)ethyl] diethylmethylammonium monochloride dihydrochloride monohydrate

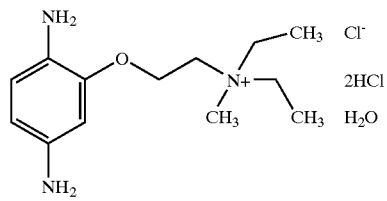

a) Preparation of [2-(2-acetylamino-5-nitrophenoxy)ethyl] diethylmethylammonium methyl sulphate The quaternization of 59.1 g (0.2 mol) of N-[2-(2-diethylaminoethoxy)-4-nitrophenyl]acetamide dissolved in 700 ml of ethyl acetate was carried but by adding 20.9 ml (0.22 mol) of dimethyl sulphate with stirring for one hour at room temperature.

The quaternized compound precipitated.

The reaction mixture was then heated for one hour at 50° C.

The crystals were filtered off, reimpasted in the minimum amount of absolute ethanol and dried at 50° C. under vacuum over phosphorus pentoxide.

71.3 g of pale yellow crystals melting at 141–145° C. (Kofler) were obtained, the elemental analysis of which, calculated for $C_{16}H_{27}N_3O_8S$, was:

| % | C | H | N | O | S |
|---|---|---|---|---|---|
| Calculated | 45.60 | 6.46 | 9.97 | 30.37 | 7.61 |
| Found | 45.18 | 6.44 | 9.84 | 30.93 | 7.49 | b) Reduction of [2-(2-acetylamino-5-nitrophenoxy)ethyl] diethylmethylammonium methyl sulphate A mixture of 100 ml of 96° ethanol, 10 ml of water, 50 g of finely powdered zinc and 1 g of ammonium chloride was heated to the reflux point of the alcohol. 42.1 g (0.1 mol) of [2-(2-acetylamino-5-nitrophenoxy)ethyl] diethylmethylammonium methyl sulphate prepared in the previous step were added portionwise so as to maintain the reflux without heating. The reaction was exothermic.

At the end of the addition, the reflux was maintained for a further 10 minutes.

The mixture was filtered while boiling and evaporated to dryness under reduced pressure.

44.4 g of a pale yellow oil of [2-(2-acetylaminophenoxy) ethyl]diethylmethylammonium methyl sulphate were obtained.

c) Deacetylation of [2-(2-acetylamino-5-aminophenoxy) ethyl]diethylmethylammonium methyl sulphate The [2-(2-acetylamino-5-aminophenoxy)ethyl]-diethylmethylammonium methyl sulphate obtained in the previous step (43.9 g) was dissolved, at room temperature and with stirring, in 100 ml of approximately 5N absolute hydrochloric ethanol.

After half an hour, a white crystalline precipitate appeared.

The suspension was heated at the reflux point of the alcohol for one hour to complete the anion exchange.

The crude product was cooled, filtered off, washed with absolute ethanol and dried at 50° C. under vacuum and over potassium hydroxide.

28.9 g of white crystals melting with decomposition at 110–120° C. (Kofler) were obtained, the elemental analysis of which, calculated for $C_{13}H_{26}N_3OCl_3 \cdot H_2O$, was:

| % | C | H | N | O | Cl |
|---|---|---|---|---|---|
| Calculated | 42.81 | 7.74 | 11.52 | 8.77 | 29.16 |
| Found | 43.18 | 7.59 | 11.30 | 8.43 | 29.80 |

Preparation Example 2

Synthesis of N,N-bis(trimethylammoniopropyl)-4-aminoaniline dichloride dihydrochloride

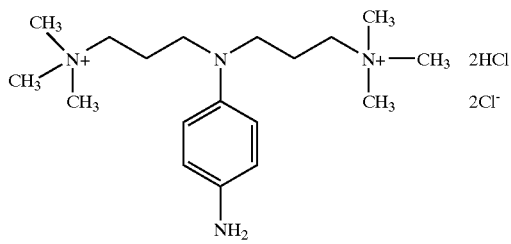

a) Preparation of N-(3-dimethylaminopropyl)-N',N'-dimethyl-N-(4-nitrophenyl)propane-1,3-diamine A mixture of 28.2 g (0.2 mol) of 1-fluoro-4-nitrobenzene, 39.4 g (0.21 mol) of N-(3-dimethylaminopropyl)-N',N'-dimethylpropane-1,3-diamine and 27.6 g (0.2 mol) of potassium carbonate in 200 ml of dimethyl sulphoxide was heated with stirring on a boiling water bath for 2 hours.

The mixture was cooled, diluted with 400 ml of water and extracted with ethyl acetate.

The extracts were washed several times with water, dried over sodium sulphate, filtered and evaporated to dryness under reduced pressure.

61.6 g of a yellow oil of the expected N-(3-dimethylaminopropyl)-N',N'-dimethyl-N-(4-nitrophenyl)propane-1,3-diamine were obtained.

b) Preparation of N,N-bis(trimethylammoniopropyl)-4-nitroaniline methyl sulphate The procedure described in Example 1, step a) above was used.

Starting with 61.6 g (0.2 mol) of N-(3-dimethylaminopropyl)-N'N'-dimethyl-N-(4-nitrophenyl)propane-1,3-diamine obtained in the previous step and 42.1 ml (0.44 mol) of methyl sulphate, 88.5 g of yellow crystals of N,N-bis(trimethylammoniopropyl)-4-nitroaniline methyl sulphate melting at 196° C. (Kofler) were obtained, the elemental analysis of which, calculated for $C_{20}H_{40}N_4O_{10}S_2$, was:

| % | C | H | N | O | S |
|---|---|---|---|---|---|
| Calculated | 42.84 | 7.19 | 9.99 | 28.54 | 11.44 |
| Found | 42.68 | 7.20 | 9.87 | 28.60 | 11.44 | c) Reduction of N,N-bis(trimethylammoniopropyl)-4-nitroaniline methyl sulphate 78.5 g (0.14 mol) of N,N-bis(trimethylammoniopropyl)-4-nitroaniline methyl sulphate, 15 g of 5% palladium on charcoal (containing 50% water), 250 ml of isopropanol and 250 ml of water were placed in a hydrogenator.

The reduction took place over half an hour under a hydrogen pressure of about 8 bar and at a temperature which was gradually raised to 70° C. After filtering off the catalyst under nitrogen, the filtrate was poured into aqueous hydrochloric acid.

The filtrate was evaporated to dryness under reduced pressure and heated in approximately 5N absolute hydrochloric ethanol to complete the anion exchange.

After drying at 40° C. under vacuum and over potassium hydroxide, 51.4 g of white crystals melting at 253–260° C. (Kofler) were obtained, the elemental analysis of which, calculated for $C_{18}H_{38}N_4Cl_4 \cdot \frac{1}{2}H_2O$, was:

| % | C | H | N | O | Cl |
|---|---|---|---|---|---|
| Calculated | 46.86 | 8.52 | 12.14 | 1.73 | 30.74 |
| Found | 46.70 | 8.42 | 11.78 | 2.30 | 30.83 |

Preparation Example 3

Synthesis of [4-(4-aminophenyl5 amino)pentyl]diethylmethylammonium monochloride dihydrochloride

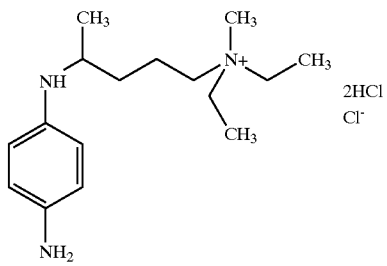

a) Preparation of N1,N1-diethyl-N4-(4-nitrophenyl)pentane-1,4-diamine

A mixture of 56.4 g (0.4 mol) of 1-fluoro-4-nitrobenzene, 79.1 g (0.5 mol) of N1,N1-diethylpentane-1,4-diamine and 33.0 g (0.24 mol) of potassium carbonate in 200 ml of water was refluxed for 5 hours with stirring.

The oily suspension was cooled and extracted with ethyl acetate.

The extracts were washed several times with water, dried over sodium sulphate, filtered and evaporated to dryness under reduced pressure.

93.4 g of a yellow oil of N1,N1-diethyl-N4-(4-nitrophenyl)pentane-1,4-diamine were obtained, the elemental analysis of which, calculated for $C_{15}H_{25}N_3O_2 \cdot \frac{1}{4}H_2O$, was:

| % | C | H | N | O |
|---|---|---|---|---|
| Calculated | 63.46 | 9.05 | 14.80 | 12.68 |
| Found | 63.61 | 8.92 | 14.68 | 12.66 | b) Preparation of diethylmethyl-[4-(4-nitrophenylamino)pentyl]ammonium methyl sulphate The procedure described for Example 1, step a) was used.

Starting with 92.7 g (0.331 mol) of N1,N1-diethyl-N4-(4-nitrophenyl)pentane-1,4-diamine obtained in the previous step and 38.0 ml (0.4 mol) of methyl sulphate, 127.2 g of an orange-coloured oil of diethylmethyl-[4-(4-nitrophenylamino)pentyl]ammonium methyl sulphate were obtained, the elemental analysis of which, calculated for $C_{17}H_{31}N_3O_6S \cdot \frac{1}{2}H_2O$, was:

| % | C | H | N | O | S |
|---|---|---|---|---|---|
| Calculated | 49.26 | 7.78 | 10.14 | 25.09 | 7.74 |
| Found | 49.40 | 7.83 | 9.79 | 25.18 | 7.99 | c) Reduction of diethylmethyl-[4-(4-nitrophenylamino)pentyl]ammonium methyl sulphate The procedure described for Example 2, step c) was used.

Starting with 126.5 g (0.312 mol) of diethylmethyl-[4-(4-nitrophenylamino)pentyl]ammonium methyl sulphate obtained in the previous step, 62.5 g of white crystals melting at 200–208° C. (Kofler) were obtained, the elemental analysis of which was in accordance with that calculated for $C_{16}H_{32}N_3C_3$.

| % | C | H | N | O | S |
|---|---|---|---|---|---|
| Calculated | 44.66 | 7.70 | 13.02 | 1.65 | 32.96 |
| Found | 45.04 | 7.69 | 12.87 | 1.52 | 33.12 |

Preparation Example 4

Synthesis of {2-[(4-aminophenyl)methylamino]ethyl}trimethylammonium monochloride dihydrochloride

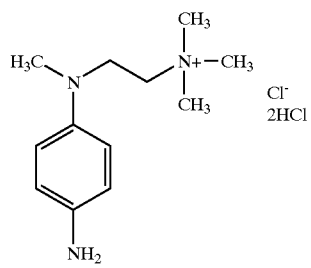

Preparation Example 5

Synthesis of [3-(4-aminophenylamino)propyl]trimethylammonium monochloride dihydrochloride

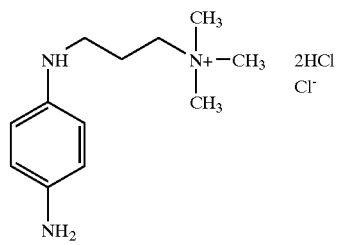

a) Preparation of trimethyl-{2-[methyl-(4-nitrophenyl)amino]ethyl}ammonium methyl sulphate The procedure described for Example 1, step a) was used.

Starting with 57.0 g (0.255 mol) of N,N,N'-trimethyl-N'-(4-nitrophenyl)ethane-1,2-diamine and 35.4 g (0.288 mol) of methyl sulphate, 84.0 g of yellow crystals of trimethyl-{2-[methyl-(4-nitrophenyl)amino]ethyl}ammonium methyl sulphate melting at 182° C. (Kofler) were obtained, the elemental analysis of which, calculated for $C_{13}H_{23}N_3O_6S$, was:

| % | C | H | N | O | S |
|---|---|---|---|---|---|
| Calculated | 44.69 | 6.64 | 12.03 | 27.47 | 9.18 |
| Found | 44.51 | 6.64 | 11.92 | 27.28 | 9.12 | b) Reduction of trimethyl-{2-[methyl-(4-nitrophenyl)amino]ethyl}ammonium methyl sulphate 69.9 g (0.2 mol) of trimethyl-{2-[methyl-(4-nitrophenyl)amino]ethyl}ammonium methyl sulphate obtained in the previous step, 20 g of 5% palladium on charcoal (containing 50% water), 250 ml of isopropanol and 250 ml of water were placed in a hydrogenator.

The reduction took place over ½ hour at a hydrogen pressure of about 8 bar and at a temperature which was gradually raised to 70° C. After filtering off the catalyst under nitrogen, the filtrate was poured into aqueous hydrochloric acid.

The filtrate was evaporated to dryness under reduced pressure and heated in approximately 5N absolute hydrochloric ethanol in order to complete the anion exchange.

After drying at 40° C. under vacuum and over potassium hydroxide, 42.6 g of pale beige-coloured crystals melting at a temperature above 260° C. (Kofler) were obtained, the elemental analysis of which, calculated for $C_{12}H_{24}N_3Cl_3 \cdot \frac{1}{3} H_2O$, was:

a) Preparation of trimethyl-[3-(4-nitrophenylamino)propyl]ammonium methyl sulphate The procedure described for Example 1, step a) was used.

Starting with 33.5 g (0.15 mol) of N,N-dimethyl-N'-(4-nitrophenyl)propane-1,3-diamine and 15.7 ml (0.165 mol) of methyl sulphate, 49.2 g of pale yellow crystals of trimethyl-[3-(4-nitrophenylamino)propyl]ammonium methyl sulphate melting at 168° C. (Kofler) were obtained, the elemental analysis of which, calculated for $C_{13}H_{23}N_3O_6S$, was:

| % | C | C | N | O | S |
|---|---|---|---|---|---|
| Calculated | 44.69 | 6.64 | 12.03 | 27.47 | 9.18 |
| Found | 44.65 | 6.72 | 12.05 | 27.48 | 9.22 | b) Reduction of trimethyl-[3-(4-nitrophenylamino)propyl]ammonium methyl sulphate The procedure described for Example 4, step b) was used.

Starting with 38.6 g (0.1105 mol) of trimethyl-[3-(4-nitrophenylamino)propyl]ammonium methyl sulphate obtained in the previous step, 25.6 g of white crystals melting with decomposition at 248° C. (Kofler) were obtained, the elemental analysis of which, calculated for $C_{12}H_{24}N_3Cl_3 \cdot \frac{1}{2}H_2O \cdot \frac{1}{2}CH_3CH_2OH$, was:

| % | C | H | N | O | Cl |
|---|---|---|---|---|---|
| Calculated | 44.77 | 8.09 | 12.05 | 4.59 | 30.50 |
| Found | 45.22 | 8.03 | 12.05 | 4.44 | 30.80 |

Preparation Example 6

Synthesis of [2-(4-aminophenylamino)ethyl] diethylmethylammonium monochloride dihydrochloride

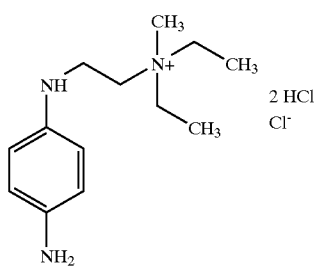

a) Preparation of diethylmethyl-[2-(4-nitrophenylamino) ethyl]ammonium methyl sulphate The procedure described for Example 1, step a) was used.

Starting with 21.5 g (0.091 mol) of N,N-diethyl-N'-(4-nitrophenyl)ethane-1,2-diamine, 21.0 g of pale yellow crystals melting at 118° C. (Kofler) were obtained, the elemental analysis of which, calculated for $C_{13}H_{22}N_3O_2S$, was:

| % | C | H | N | O | S |
|---|---|---|---|---|---|
| Calculated | 46.27 | 6.73 | 11.56 | 26.41 | 8.82 |
| Found | 45.99 | 7.01 | 11.46 | 26.63 | 8.91 | b) Reduction of diethylmethyl-[2-(4-nitrophenylamino) ethyl]ammonium methyl sulphate The reduction was carried out according to the procedure described above in Example 1, step b).

Starting with 20.0 g (0.055 mol) of diethylmethyl-[2-(4-nitrophenylamino)ethyl]ammonium methyl sulphate and after heating in approximately 5N absolute hydrochloric ethanol in order to complete the anion exchange, 14.0 g of white crystals melting with decomposition at 231° C. (Kofler) were obtained, the elemental analysis of which, calculated for $C_{13}H_{26}N_3Cl_2\cdot\frac{1}{2}H_2O$, was:

| % | C | H | N | O | Cl |
|---|---|---|---|---|---|
| Calculated | 45.96 | 8.01 | 12.37 | 2.35 | 31.31 |
| Found | 46.58 | 7.81 | 12.37 | 1.30 | 31.94 |

Preparation Example 7

Synthesis of [4-(4-aminophenylamino)pentyl] diethyl-(2-hydroxyethyl)ammonium monochloride dihydrochloride monohydrate

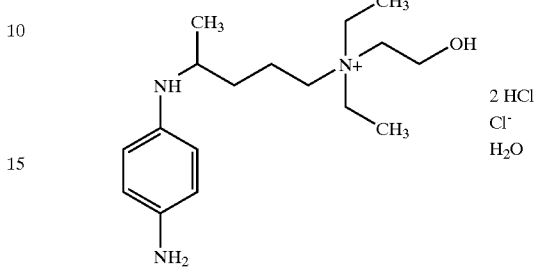

a) Preparation of [4-(4-nitrophenylamino)pentyl]-diethyl-(2-hydroxyethyl)ammonium chloride A solution of 111.7 g (0.40 mol) of N1,N1-diethyl-N4-(4-nitrophenyl)pentane-1,4-diamine obtained in step a) of Preparation Example 3 described above in 222 ml of 1-chloroethanol was refluxed for 7 hours.

The 1-chloroethanol was evaporated off under reduced pressure and the orange-coloured oil was taken up in 200 ml of absolute ethanol.

The crystalline compound was filtered off and purified by recrystallization from refluxing 96° ethanol.

69.5 g of pale yellow crystals of [4-(4-nitrophenylamino) pentyl]diethyl-(2-hydroxyethyl)ammonium chloride melting at 176° C. (Kofler) were obtained, the elemental analysis of which, calculated for $C_{17}H_{30}N_3O_3Cl$, was:

| % | C | H | N | O | Cl |
|---|---|---|---|---|---|
| Calculated | 56.74 | 8.40 | 11.68 | 13.34 | 9.85 |
| Found | 56.95 | 8.40 | 11.76 | 13.37 | 9.82 | b) Reduction of [4-(4-nitrophenylamino)pentyl]diethyl(2-hydroxyethyl)ammonium chloride The procedure described above in Example 2, step c) was used.

Starting with 66.6 g (0.185 mol) of [4-(4-nitrophenylamino)pentyl]diethyl-(2-hydroxyethyl) ammonium chloride obtained above in the previous step, 54.0 g of white crystals of [4-(4-aminophenylamino)pentyl] diethyl-(2-hydroxyethyl)ammonium chloride dihydrochloride monohydrate melting at 181° C. (Kofler) were obtained, the elemental analysis of which, calculated for $C_{17}H_{34}N_3OCl_3\cdot H_2O$, was:

| % | C | H | N | O | Cl |
|---|---|---|---|---|---|
| Calculated | 48.52 | 8.62 | 9.98 | 7.60 | 25.27 |
| Found | 48.11 | 8.63 | 9.87 | 8.25 | 25.51 |

Preparation Example 8

Synthesis of 1-{[5-amino-2-(2-hydroxyethylamino)phenylcarbamoyl]methyl}-1,4-dimethyl-1-piperazinium chloride trihydrochloride

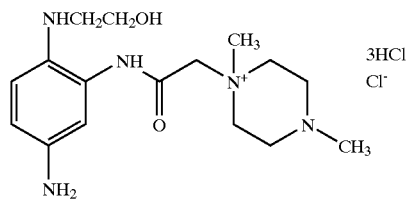

a) Preparation of 2-chloro-N-2-(2-hydroxyethylamino)-5-nitrophenyl]acetamide 82.5 g (0.418 mol) of 2-(2-amino-4-nitrophenylamino)ethanol were dissolved in 400 ml of dimethylformamide and 34.6 g (0.25 mol) of potassium carbonate were added.

The mixture was cooled to 5° C. and 34.7 ml (0.46 mol) of chloroacetyl chloride were added dropwise while keeping the temperature between 5 and 12° C.

The reaction medium was stirred for, a further one hour and poured into a mixture of 2 liters of ice-cold water and 100 ml of 36% hydrochloric acid.

The crystalline precipitate was filtered off and purified by recrystallization from refluxing acetonitrile.

77.7 g of yellow crystals of 2-chloro-N-[2-(2-hydroxyethylamino)-5-nitrophenyl]acetamide melting at 206° C. (Kofler) were obtained, the elemental analysis of which, calculated for $C_{10}H_{12}N_3O_4Cl$, was:

| %          | C     | H    | N     | O     | Cl    |
|------------|-------|------|-------|-------|-------|
| Calculated | 43.89 | 4.42 | 15.35 | 23.38 | 12.95 |
| Found      | 43.83 | 4.63 | 15.23 | 22.87 | 13.00 | b) Preparation of 1-{[2-(2-hydroxyethylamino)-5-nitrophenylcarbamoyl]methyl}-1,4-dimethyl-1-piperazinium chloride A mixture of 33.0 g (0.12 mol) of 2-chloro-N-[2-(2-hydroxyethylamino)-5-nitrophenyl]acetamide obtained above in the previous step and 27.4 g (0.24 mol) of 1,4-dimethylpiperazine in 300 ml of isobutanol was refluxed for 3 hours.

The mixture was allowed to cool to room temperature and the crystalline compound was filtered off and recrystallized from refluxing 96° ethanol.

33.8 g of pale yellow crystals of 1-{[2-(2-hydroxyethylamino)-5-nitrophenylcarbamoyl]methyl}-1,4-dimethyl-1-piperazinium chloride melting above 260° C. (Kofler) were obtained, the elemental analysis of which was in accordance with that calculated for $C_{16}H_{26}N_5O_4Cl$.

c) Reduction of 1-{[2-(2-hydroxyethylamino)-5-nitrophenylcarbamoyl]methyl}-1,4-dimethyl-1-piperazinium chloride The procedure described above in Example 2, step c) was used.

Starting with 33.0 g (0.085 mol) of 1-{[2-(2-hydroxyethylamino)-5-nitrophenylcarbamoyl]methyl}-1,4-dimethyl-1-piperazinium chloride obtained above in the previous step, 29.3 g of white crystals of 1-{[5-amino-2-(2-hydroxyethylamino)phenylcarbamoyl]methyl}-1,4-dimethyl-1-piperazinium chloride trihydrochloride melting with decomposition at 250–260° C. (Kofler) were obtained, the $^1$H NMR of which was in accordance with that of the expected product.

Preparation Example 9

Synthesis of [2-(4-aminophenylamino)propyl]trimethylammonium chloride dihydrochloride ethanol

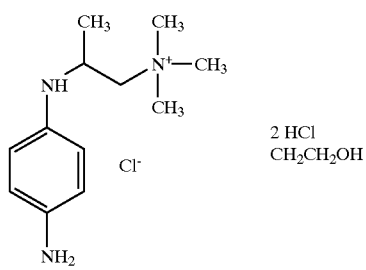

a) Preparation of trimethyl-[2-(4-nitrophenylamino)propyl]ammonium

A mixture of 141.1 g (1 mol) of 1-fluoro-4-nitrobenzene, 122.6 g (1.2 mol) of N1,N1-dimethyl-propane-1,2-diamine and 82.8 g (0.6 mol) of potassium carbonate in 400 ml of water was refluxed for 10 hours.

The mixture was cooled to room temperature, the aqueous phase was removed and the orange-coloured oil was taken up in ethyl acetate.

After washing with water, drying over anhydrous sodium sulphate, filtration and evaporation to dryness under reduced pressure, 209.0 g of orange-coloured crystals melting below 50° C. (Kofler) were obtained.

b) Preparation of trimethyl-[2-(4-nitrophenylamino)propyl]ammonium methyl sulphate 111.6 g (0.5 mol) of trimethyl-[2-(4-nitrophenylamino)propyl]ammonium obtained in the previous step were dissolved in one liter of ethyl acetate at room temperature and 57.1 ml (0.6 mol) of methyl sulphate were added dropwise.

The mixture was heated for ½ hour at 60–65° C. with stirring.

The crystalline precipitate was filtered off, washed with ethyl acetate and dried under vacuum at 45° C.

160.9 g of pale yellow crystals of trimethyl-[2-(4-nitrophenylamino)propyl]ammonium methyl sulphate melting at 235° C. were obtained, the elemental analysis of which, calculated for $C_{13}H_{23}N_3O_6S$, was:

| %          | C     | H    | N     | O     | S    |
|------------|-------|------|-------|-------|------|
| Calculated | 44.69 | 6.64 | 12.03 | 27.47 | 9.18 |
| Found      | 44.62 | 6.67 | 11.92 | 27.42 | 9.21 | c) Reduction of trimethyl-[2-(4-nitrophenylamino)propyl]ammonium methyl sulphate The procedure described above in Example 2, step c) was used.

Starting with 104.8 g (0.3 mol) of trimethyl-[2-(4-nitrophenylamino)propyl]ammonium methyl sulphate obtained above in the previous step, 72.0 g of white crystals of [2-(4-aminophenylamino)propyl]trimethylammonium chloride dihydrochloride ethanol melting with decomposition above 260° C. (Kofler) were obtained, the elemental analysis of which, calculated for $C_{12}H_{24}N_3Cl_3 \cdot C_2H_5OH$, was:

| % | C | H | N | O |
|---|---|---|---|---|
| Calculated | 46.35 | 8.34 | 11.58 | 4.41 |
| Found | 46.06 | 8.36 | 11.33 | 5.09 |

APPLICATION EXAMPLES

Examples 1 to 5 of Dyeing in Basic Medium

The following dye compositions were prepared (contents in grams):

| | EXAMPLE | | | | |
|---|---|---|---|---|---|
| | 1 | 2 | 3 | 4 | 5 |
| [2-(2,5-Diaminophenoxy)-ethyl]diethylmethylammonium monochloride dihydrochloride monohydrate (compound of formula (I)) | 1.08 | 1.08 | 1.08 | 1.08 | 1.08 |
| Resorcinol (coupler) | — | 0.33 | — | — | — |
| meta-Aminophenol (coupler) | — | — | 0.327 | — | — |
| 2-Methyl-5-N-(β-hydroxyethyl)aminophenol (coupler) | — | — | — | 0.543 | — |
| 2,4-Diaminophenoxyethanol dihydrochloride (coupler) | — | — | — | — | 0.675 |
| Common dye support | (*) | (*) | (*) | (*) | (*) |
| Demineralized water qs | 100 g | 100 g | 100 g | 100 g | 100 g |

(*) Common dye support:
96° Ethanol 20 g
Pentasodium salt of diethylenetriamine-pentaacetic acid sold under the name Masquol DTPA by the company Protex 1.08 g
Sodium metabisulphite as an aqueous solution containing 35% A.M. 0.58 g A.M.
20% Aqueous ammonia 10 g At the time of use, each of the above dye compositions was mixed, weight for weight, with a 20-volumes hydrogen peroxide solution (6% by weight) of pH 3.

The mixture obtained was applied to locks of natural or permanent-waved grey hair containing 90% white hairs, for 30 minutes. The locks were then rinsed, washed with a standard shampoo, rinsed again and then dried.

The shades obtained are given in the table below:

| EXAMPLE | DYEING pH | Shade on natural hair | Shade on permanent-waved hair |
|---|---|---|---|
| 1 | 10 ± 0.2 | Iridescent ash beige-blond | Iridescent ash dark blond |
| 2 | 10 ± 0.2 | Pearlescent dark blond | Purple iridescent chestnut |
| 3 | 10 ± 0.2 | Ash purple | Ash purple |
| 4 | 10 ± 0.2 | Iridescent purple | Iridescent purple |
| 5 | 10 ± 0.2 | Blue | Blue |

Examples 6 to 8 of Dyeing in Basic Medium

The following dye compositions were prepared (contents in grams):

| | EXAMPLE | | |
|---|---|---|---|
| | 6 | 7 | 8 |
| [2-(4-Aminophenylamino)propyl]-trimethylammonium chloride dihydrochloride ethanol (compound of formula (I)) | 1.09 | — | — |
| [4-(4-Aminophenylamino)pentyl] diethyl-(2-hydroxyethyl)ammonium monochloride dihydrochloride monohydrate (compound of formula (I)) | — | 1.26 | — |
| 1{[5-Amino-2-(2-hydroxyethyl-amino)phenylcarbamoyl]methyl}-1,4-dimethyl-1-piperazinium chloride trihydrochloride (compound of formula (I)) | — | — | 1.40 |
| 6-Hydroxybenzomorpholine (coupler) | 0.453 | — | — |
| 1,3-Dihydroxy-2-methylbenzene (coupler) | — | 0.327 | — |
| 3-Aminophenol (coupler) | — | — | 0.327 |
| Common dye support | (*) | (*) | (*) |
| Demineralized water qs | 100 g | 100 g | 100 g |

(*) Common dye support:
This is identical to the one used for the above Dyeing Examples 1 to 5.

At the time of use, each of the above dye compositions was mixed, weight for weight, with a 20-volumes hydrogen peroxide solution (6% by weight) of pH 3.

The mixture obtained was applied to locks of natural grey hair containing 90% white hairs, for 30 minutes. The locks were then rinsed, washed with a standard shampoo, rinsed again and then dried.

The shades obtained are given in the table below:

| EXAMPLE | Dyeing pH | Shade obtained |
|---|---|---|
| 6 | 10 ± 0.2 | Golden mahogany |
| 7 | 10 ± 0.2 | Iridescent grey dark blond |
| 8 | 10 ± 0.2 | Golden beige very light blond |

What is claimed is:
1. A compound of formula (I), or an acid addition salt thereof:

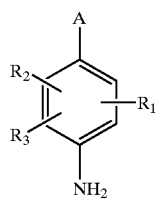

(1)

wherein:
$R_1$, $R_2$ and $R_3$, are identical or different and represent
a hydrogen atom;
a halogen atom;
a group Z;
a $(C_1-C_6)$alkylcarbonyl radical;
an amino$(C_1-C_6)$alkylcarbonyl radical;
an N-Z-amino$(C_1-C_6)$alkylcarbonyl radical;
an N-$(C_1-C_6)$alkylamino$(C_1-C_6)$alkylcarbonyl radical;
an N,N-di$(C_1-C_6)$alkylamino$(C_1-C_6)$alkylcarbonyl radical;
an amino$(C_1-C_6)$alkylcarbonyl$(C_1-C_6)$alkyl radical;

an N-Z-amino($C_1$–$C_6$)alkylcarbonyl($C_1$–$C_6$)alkyl radical;
an N-($C_1$–$C_6$)alkylamino($C_1$–$C_6$)alkylcarbonyl($C_1$–$C_6$)alkyl radical;
an N,N-di($C_1$–$C_6$)alkylamino($C_1$–$C_6$)alkylcarbonyl($C_1$–$C_6$)alkyl radical;
a carboxyl radical;
a ($C_1$–$C_6$)alkylcarboxyl radical;
a $C_1$–$C_6$ alkylsulfonoyl radical;
an aminosulfonyl radical;
an N-Z-aminosulfonyl radical;
a $C_1$–$C_6$ N-alkylaminosulphonyl radical;
an N,N-di($C_1$–$C_6$)alkylaminosulphonyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a carbamyl radical;
an N-($C_1$–$C_6$)alkylcarbamyl radical;
an N,N-di($C_1$–$C_6$)alkylcarbamyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a $C_1$–$C_6$ alkyl radical;
a monohydroxy($C_1$–$C_6$)alkyl radical;
a polyhydroxy($C_2$–$C_6$)alkyl radical;
a ($C_1$–$C_6$)alkoxy($C_1$–$C_6$)alkyl radical;
a trifluoro($C_1$–$C_6$)alkyl radical;
a cyano radical;
a group $OR_6$;
a group $SR_6$;
an amino group protected with a ($C_1$–$C_6$)alkylcarbonyl, ($C_1$–$C_6$)alkylcarboxyl, trifluoro($C_1$–$C_6$)alkylcarbonyl, amino($C_1$–$C_6$)alkylcarbonyl, N-Z-amino($C_1$–$C_6$)alkylcarbonyl, N-($C_1$–$C_6$)alkylamino($C_1$–$C_6$)alkylcarbonyl, N,N-di($C_1$–$C_6$)alkylamino($C_1$–$C_6$)alkylcarbonyl, carbamyl, N-($C_1$–$C_6$)alkylcarbamyl, N,N-di($C_1$–$C_6$)alkylcarbamyl, $C_1$–$C_6$ alkylsulphonyl, aminosulphonyl, N-Z-aminosulphonyl, $C_1$–$C_6$ N-alkylaminosulphonyl, N,N-di($C_1$–$C_6$)alkylaminosulphonyl, thiocarbamyl or formyl radical, or with a group Z;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_1$–$C_6$)alkyl, $C_1$–$C_6$ alkylcarbonyl, carbamyl, N-($C_1$–$C_6$)alkylcarbamyl, N,N-di($C_1$–$C_6$)alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or with a group Z;

$R_6$ represents
a $C_1$–$C_6$ alkyl radical;
a monohydroxy($C_1$–$C_6$)alkyl radical;
a polyhydroxy($C_2$–$C_6$)alkyl radical;
a group Z;
a ($C_1$–$C_6$)alkoxy($C_1$–$C_6$)alkyl radical;
an aryl radical;
a benzyl radical;
a carboxy($C_1$–$C_6$)alkyl radical;
a ($C_1$–$C_6$)alkylcarboxy($C_1$–$C_6$)alkyl radical;
a cyano($C_1$–$C_6$)alkyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a trifluoro($C_1$–$C_6$)alkyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a ($C_1$–$C_6$)alkylsulphinyl($C_1$–$C_6$)alkyl radical;
a ($C_1$–$C_6$)alkylsulphonyl($C_1$–$C_6$)alkyl radical;
a ($C_1$–$C_6$)alkylcarbonyl($C_1$–$C_6$)alkyl radical;
an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_1$–$C_6$)alkyl, ($C_1$–$C_6$)alkylcarbonyl, formyl, trifluoro($C_1$–$C_6$)alkylcarbonyl, ($C_1$–$C_6$)alkylcarboxyl, carbamyl, N-($C_1$–$C_6$)alkylcarbamyl, N,N-di($C_1$–$C_6$)alkylcarbamyl, thiocarbamyl and $C_1$–$C_6$ alkylsulphonyl radicals, and the group Z;

A represents a group —$NR_4R_5$ or a hydroxyl radical;
$R_4$ and $R_5$, are identical or different and represent
a hydrogen atom;
a group Z;
a $C_1$–$C_6$ alkyl radical;
a monohydroxy($C_1$–$C_6$)alkyl radical;
a polyhydroxy($C_2$–$C_6$)alkyl radical;
a ($C_1$–$C_6$)alkoxy($C_1$–$C_6$)alkyl radical;
an aryl radical;
a benzyl radical;
a cyano($C_1$–$C_6$)alkyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a thiocarbamyl($C_1$–$C_6$)alkyl radical;
a trifluoro($C_1$–$C_6$)alkyl radical;
a sulpho($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a ($C_1$–$C_6$)alkylcarbonyl($C_1$–$C_6$)alkyl radical;
an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_1$–$C_6$)alkyl, ($C_1$–$C_6$)alkylcarbonyl, carbamyl, N-($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z;

Z represents a group of formula (II) below:

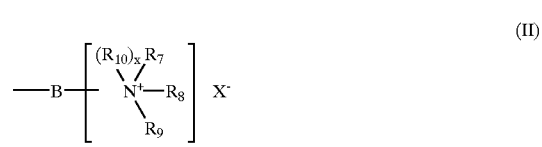

(II)

wherein:
B is a divalent linker arm which represents a linear or branched alkyl chain, said alkyl chain being uninterrupted or interrupted by one or more hetero atoms, and said alkyl chain being unsubstituted or substituted with one or more hydroxyl or $C_1$–$C_6$ alkoxy radicals, and which said chain has no ketone functions or at least one ketone function;

$R_7$, $R_8$ and $R_9$, are identical or different and represent
  a $C_1$–$C_6$ alkyl radical,
  a monohydroxy($C_1$–$C_6$)alkyl radical,
  a polyhydroxy($C_2$–$C_6$)alkyl radical,
  a ($C_1$–$C_6$)alkoxy($C_1$–$C_6$)alkyl radical,
  a cyano($C_1$–$C_6$)alkyl radical,
  an aryl radical,
  a benzyl radical,
  a carbamyl($C_1$–$C_6$)alkyl radical,
  a tri($C_1$–$C_6$)alkylsilane($C_1$–$C_6$)alkyl radical, or
  an amino($C_1$–$C_6$)alkyl radical wherein the amine is protected with a ($C_1$–$C_6$)alkylcarbonyl, carbamyl or $C_1$–$C_6$ alkylsulphonyl radical; or
  two of the radicals $R_7$, $R_8$ and $R_9$ together form, with the nitrogen atom to which they are attached, a saturated 5- or 6-membered carbon ring, wherein said ring may contain one or more additional hetero atoms, wherein said ring is unsubstituted or substituted with
    a halogen atom,
    a hydroxyl radical,
    a $C_1$–$C_6$ alkyl radical,
    a monohydroxy($C_1$–$C_6$)alkyl radical,
    a polyhydroxy($C_2$–$C_6$)alkyl radical,
    a nitro radical,
    a cyano radical,
    a cyano($C_1$–$C_6$)alkyl radical,
    a $C_1$–$C_6$ alkoxy radical,
    a tri($C_1$–$C_6$)alkylsilane($C_1$–$C_6$)alkyl radical,
    an amido radical,
    an aldehydo radical,
    a carboxyl radical,
    a ($C_1$–$C_6$)alkylcarbonyl radical,
    a thio radical,
    a thio($C_1$–$C_6$)alkyl radical,
    a $C_1$–$C_6$ alkylthio radical,
    an amino radical, or
    an amino radical protected with a ($C_1$–$C_6$) alkylcarbonyl, carbamyl or $C_1$–$C_6$ alkylsulphonyl radical; and/or
  one of $R_7$, $R_8$ and $R_9$ may represent a second group Z which is identical to or different from the first group Z;

$X^-$ represents a monovalent or divalent anion;

$R_{10}$ represents
  a $C_1$–$C_6$ alkyl radical;
  a monohydroxy($C_1$–$C_6$)alkyl radical;
  a polyhydroxy($C_2$–$C_6$)alkyl radical;
  an aryl radical;
  a benzyl radical;
  an amino($C_1$–$C_6$)alkyl radical,
  an amino($C_1$–$C_6$)alkyl radical wherein the amine is protected with a ($C_1$–$C_6$)alkylcarbonyl, carbamyl or $C_1$–$C_6$ alkylsulphonyl radical;
  a carboxy($C_1$–$C_6$)alkyl radical;
  a cyano($C_1$–$C_6$)alkyl radical;
  a carbamyl($C_1$–$C_6$)alkyl radical;
  a trifluoro($C_1$–$C_6$)alkyl radical;
  a tri($C_1$–$C_6$)alkylsilane($C_1$–$C_6$)alkyl radical;
  a sulphonamido($C_1$–$C_6$)alkyl radical;
  a ($C_1$–$C_6$)alkylcarboxy($C_1$–$C_6$)alkyl radical;
  a ($C_1$–$C_6$)alkylsulphinyl($C_1$–$C_6$)alkyl radical;
  a ($C_1$–$C_6$)alkylsulphonyl($C_1$–$C_6$)alkyl radical;
  a ($C_1$–$C_6$)alkylketo($C_1$–$C_6$)alkyl radical;
  an N-($C_1$–$C_6$)alkylcarbamyl($C_1$–$C_6$)alkyl radical;
  an N-($C_1$–$C_6$)alkylsulphonamido($C_1$–$C_6$)alkyl radical;

x is an integer equal to 0 or 1; with the proviso that:
  when x=0, then the divalent linker arm B is attached to the nitrogen atom bearing the radicals $R_7$ to $R_9$,
  when x=1, then two of the radicals $R_7$ to $R_9$ form, together with the nitrogen atom to which they are attached, a saturated 5- or 6-membered ring as defined above, and the linker arm B is attached to a carbon atom of said saturated ring;

with the proviso that:
  the number of cationic groups Z in said compound or acid addition salt thereof is at least equal to 1;
  when A represents a group —$NR_4R_5$, and when $R_4$ or $R_5$ represents a group Z, and when the divalent linker arm B represents an alkyl chain containing a ketone function, then said ketone function is not directly attached to the nitrogen atom of the group —$NR_4R_5$;

and further with the proviso that
  4-amino-2-fluoro-N-(trimethylammonioethyl)aniline iodide;
  4-amino-2-trifluoromethyl-N-(trimethylammonioethyl) aniline iodide;
  4-amino-2-cyano-N-(trimethylammonioethyl)aniline iodide;
  2-(4-aminophenylamino)ethyltrimethylammonium iodide;
  4-amino-3-methyl-N-ethyl-N-(trimethylammonioethyl) aniline chloride;

compounds of formula (I) wherein A is a hydroxyl radical, two of said $R_1$, $R_2$ and $R_3$ are each a hydrogen atom, the other of said $R_1$, $R_2$ and $R_3$ is a group Z wherein x=0, B is —$CH_2$—, and one and only one of said $R_7$, $R_8$ and $R_9$ is chosen from 3-hydroxyphenyl radicals and 3-aminophenyl radicals;

compounds of formula (I) wherein $R_1$, $R_2$ and $R_3$ are each a hydrogen atom, x=0, A is a group —$NR_4R_5$ wherein one of said $R_4$ and $R_5$ is a hydrogen atom and the other of said $R_4$ and $R_5$ is a group Z wherein B is $C_1$–$C_6$ alkyl, one of said $R_7$, $R_8$ and $R_9$ is chosen from $C_1$–$C_4$ alkyl, monohydroxy ($C_1$–$C_4$)alkyl, and ($C_1$–$C_4$)alkoxy ($C_1$–$C_4$)alkyl groups; and the other two of said $R_7$, $R_8$ and $R_9$ are chosen from $C_1$–$C_6$ alkyl groups;

compounds of formula (I) wherein two of said $R_1$, $R_2$, and $R_3$ are each a hydrogen, the other of said $R_1$, $R_2$, and $R_3$ is a —$CH_3$ radical, $X^-$ is a bromide anion, A is —$NR_4R_5$, wherein $R_4$ is a —$CH_2CH_3$ radical and $R_5$ is a Z group, wherein, x=0, B is —$C_2H_4NHCOCH_2$—, and $R_7$, $R_8$, and $R_9$ are each a —$CH_2CH_3$ radical;

compounds of formula (I), wherein said $R_1$, $R_2$, and $R_3$ are each a hydrogen, $X^-$ is a chloride anion, A is —$NR_4R_5$, wherein $R_4$ is a —$CH_2CH_3$ radical and $R_5$ is a Z group, wherein, x=0, B is —$CH_2CH_2$—, and $R_7$, $R_8$, and $R_9$ are each a —$CH_3$ radical;

and acid addition salts thereof are excluded.

2. A compound of the formula (I) or acid addition salt thereof according to claim 1, wherein said divalent linker B represents a linear alkyl chain containing from 1 to 14 carbon atoms, or a branched alkyl chain containing from 3 to 14 carbon atoms, and wherein said hetero atoms in said divalent linker B are selected from oxygen, sulphur and nitrogen atoms; and further wherein when two of the radicals R7, R8 and R9 together form, with the nitrogen atom to which they are attached, a saturated 5- or 6-membered ring, said ring is selected from a quaternized pyrrolidine, a piperidine, a piperazine, or a morpholine ring.

3. A compound of the formula (I) or acid addition salt thereof according to claim 1, wherein X⁻ represents a halogen atom, a hydroxide, a hydrogenosulphate, or a C1–C6 alkyl sulphate.

4. A compound of the formula (I) or acid addition salt thereof according to claim 3, wherein said halogen atom is chlorine, bromine, fluorine or iodine.

5. A compound according to claim 1, wherein said compound is:
[2-(2,5-diaminophenoxy)ethyl]diethylmethylammonium chloride monohydrate;
N,N-bis(trimethylammoniopropyl)-4-aminoaniline dichloride;
{2-[(4-aminophenyl)methylamino]ethyl}trimethylammonium chloride;
[4-(4-amino-2-methylphenylamino)pentyl]diethylmethylammonium chloride;
[4-(4-amino-3-methylphenylamino)pentyl]diethylmethylammonium chloride;
1-{[5-amino-2-(2-hydroxyethylamino)phenylcarbamoyl]methyl}-1,4-dimethyl-1-piperazinium chloride;
or an acid addition salt thereof.

6. A compound according to claim 5, wherein said compound is:
[2-(2,5-diaminophenoxy)ethyl]diethylmethylammonium chloride monohydrate;
N,N-bis(trimethylammoniopropyl)-4-aminoaniline chloride;
{2-[(4-aminophenyl)methylamino]ethyl}trimethylammonium chloride;
or an acid addition salt thereof.

7. A method of dyeing keratin fibers comprising applying to said keratin fibers at least one oxidation base selected from compounds of formula (1) and acid addition salts thereof:

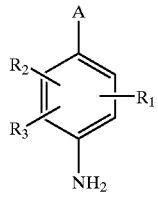

(1)

wherein:
$R_1$, $R_2$ and $R_3$, are identical or different and represent
a hydrogen atom;
a halogen atom;
a group Z;
a ($C_1$–$C_6$)alkylcarbonyl radical;
an amino($C_1$–$C_6$)alkylcarbonyl radical;
an N-Z-amino($C_1$–$C_6$)alkylcarbonyl radical;
an N-($C_1$–$C_6$)alkylamino($C_1$–$C_6$)alkylcarbonyl radical;
an N,N-di($C_1$–$C_6$)alkylamino($C_1$–$C_6$)alkylcarbonyl radical;
an amino($C_1$–$C_6$)alkylcarbonyl($C_1$–$C_6$)alkyl radical;
an N-Z-amino($C_1$–$C_6$)alkylcarbonyl($C_1$–$C_6$)alkyl radical;
an N-($C_1$–$C_6$)alkylamino($C_1$–$C_6$)alkylcarbonyl ($C_1$–$C_6$)alkyl radical;
an N,N-di($C_1$–$C_6$)alkylamino($C_1$–$C_6$)alkylcarbonyl ($C_1$–$C_6$)alkyl radical;
a carboxyl radical;
a ($C_1$–$C_6$)alkylcarboxyl radical;
a $C_1$–$C_6$ alkylsulphonyl radical;
an aminosulphonyl radical;
an N-Z-aminosulphonyl radical;
a $C_1$–$C_6$ N-alkylaminosulphonyl radical;
an N,N-di($C_1$–$C_6$)alkylaminosulphonyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a carbamyl radical;
an N-($C_1$–$C_6$)alkylcarbamyl radical;
an N,N-di($C_1$–$C_6$)alkylcarbamyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a $C_1$–$C_6$ alkyl radical;
a monohydroxy($C_1$–$C_6$)alkyl radical;
a polyhydroxy($C_2$–$C_6$)alkyl radical;
a ($C_1$–$C_6$)alkoxy($C_1$–$C_6$)alkyl radical;
a trifluoro($C_1$–$C_6$)alkyl radical;
a cyano radical;
a group $OR_6$;
a group $SR_6$;
an amino group protected with a ($C_1$–$C_6$)alkylcarbonyl, ($C_1$–$C_6$)alkylcarboxyl, trifluoro($C_1$–$C_6$)alkylcarbonyl, amino($C_1$–$C_6$)alkylcarbonyl, N-Z-amino($C_1$–$C_6$)alkylcarbonyl, N-($C_1$–$C_6$)alkylamino($C_1$–$C_6$)alkylcarbonyl, N,N-di($C_1$–$C_6$)alkylamino($C_1$–$C_6$)alkylcarbonyl, carbamyl, N-($C_1$–$C_6$)alkylcarbamyl, N,N-di($C_1$–$C_6$)alkylcarbamyl, $C_1$–$C_6$ alkylsulphonyl, aminosulphonyl, N-Z-aminosulphonyl, $C_1$–$C_6$ N-alkylaminosulphonyl, N,N-di($C_1$–$C_6$)alkylaminosulphonyl, thiocarbamyl or formyl radical, or with a group Z;
an amino($C_1$–$C_6$)alkyl radical wherein the amine is substituted with one or two identical or different radicals selected from $C_1$–$C_6$ alkyl, monohydroxy ($C_1$–$C_6$)alkyl, polyhydroxy($C_2$–$C_6$)alkyl, $C_1$–$C_6$ alkylcarbonyl, carbamyl, N-($C_1$–$C_6$)alkylcarbamyl, N,N-di($C_1$–$C_6$)alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or with a group Z;

$R_6$ represents
a $C_1$–$C_6$ alkyl radical;
a monohydroxy($C_1$–$C_6$)alkyl radical;
a polyhydroxy($C_2$–$C_6$)alkyl radical;
a group Z;
a ($C_1$–$C_6$)alkoxy($C_1$–$C_6$)alkyl radical;
an aryl radical;
a benzyl radical;
a carboxy($C_1$–$C_6$)alkyl radical;
a ($C_1$–$C_6$)alkylcarboxy($C_1$–$C_6$)alkyl radical;
a cyano($C_1$–$C_6$)alkyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a trifluoro($C_1$–$C_6$)alkyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a ($C_1$–$C_6$)alkylsulphinyl($C_1$–$C_6$)alkyl radical;
a ($C_1$–$C_6$)alkylsulphonyl($C_1$–$C_6$)alkyl radical;
a ($C_1$–$C_6$)alkylcarbonyl($C_1$–$C_6$)alkyl radical;

an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_1$–$C_6$)alkyl, ($C_1$–$C_6$) alkylcarbonyl, formyl, trifluoro($C_1$–$C_6$)alkylcarbonyl, ($C_1$–$C_6$)alkylcarboxyl, carbamyl, N-($C_1$–$C_6$)alkylcarbamyl, N,N-di($C_1$–$C_6$)alkylcarbamyl, thiocarbamyl and $C_1$–$C_6$ alkylsulphonyl radicals, and the group Z;

A represents a group —$NR_4R_5$ or a hydroxyl radical;
$R_4$ and $R_5$, are identical or different and represent
a hydrogen atom;
a group Z;
a $C_1$–$C_6$ alkyl radical;
a monohydroxy($C_1$–$C_6$)alkyl radical;
a polyhydroxy($C_2$–$C_6$)alkyl radical;
a ($C_1$–$C_6$)alkoxy($C_1$–$C_6$)alkyl radical;
an aryl radical;
a benzyl radical;
a cyano($C_1$–$C_6$)alkyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a thiocarbamyl($C_1$–$C_6$)alkyl radical;
a trifluoro($C_1$–$C_6$)alkyl radical;
a sulpho($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radial;
an N,N-di($C_1$–$C_6$)alkylaminosulphonyl($C_1$–$C_6$)alkyl radical;
a ($C_1$–$C_6$)alkylcarbonyl($C_1$–$C_6$)alkyl radical;
an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_1$–$C_6$)alkyl, ($C_1$–$C_6$) alkylcarbonyl, carbamyl, N-($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z;

Z represents a group of formula (II) below:

(II)

wherein:
B is a divalent linker arm which represents a linear or branched alkyl chain, said alkyl chain being uninterrupted or interrupted by one or more hetero atoms, and said alkyl chain being unsubstituted or substituted with one or more hydroxyl or $C_1$–$C_6$ alkoxy radicals, and which said chain has no ketone functions or at least one ketone function;

$R_7$, $R_8$ and $R_9$, are identical or different and represent
a $C_1$–$C_6$ alkyl radical,
a monohydroxy($C_1$–$C_6$)alkyl radical,
a polyhydroxy($C_2$–$C_6$)alkyl radical,
a ($C_1$–$C_6$)alkoxy($C_1$–$C_6$)alkyl radical,
a cyano($C_1$–$C_6$)alkyl radical,
an aryl radical,
a benzyl radical,
a carbamyl($C_1$–$C_6$)alkyl radical,
a tri($C_1$–$C_6$)alkylsilane($C_1$–$C_6$)alkyl radical, or
an amino($C_1$–$C_6$)alkyl radical wherein the amine is protected with a ($C_1$–$C_6$)alkylcarbonyl, carbamyl or $C_1$–$C_6$alkylsulphonyl radical; or two of the radicals $R_7$, $R_8$ and $R_9$ together form, with the nitrogen atom to which they are attached, a saturated 5- or 6-membered carbon ring, wherein said ring may contain one or more additional hetero atoms, wherein said ring is unsubstituted or substituted with
a halogen atom,
a hydroxyl radical,
a $C_1$–$C_6$ alkyl radical,
a monohydroxy($C_1$–$C_6$)alkyl radical,
a polyhydroxy($C_1$–$C_6$)alkyl radical,
a nitro radical,
a cyano radical,
a cyano($C_1$–$C_6$)alkyl radical,
a $C_1$–$C_6$ alkoxy radical;
a tri($C_1$–$C_6$)alkylsilane($C_1$–$C_6$)alkyl radical,
an amido radical,
an aldehydo radical,
a carboxyl radical,
a ($C_1$–$C_6$)alkylcarbonyl radical,
a thio radical,
a thio($C_1$–$C_6$)alkyl radical,
a $C_1$–$C_6$ alkylthio radical,
an amino radical, or
an amino radical protected with a ($C_1$–$C_6$) alkylcarbonyl, carbamyl or $C_1$–$C_6$ alkylsulphonyl radical; and/or,
one of $R_7$, $R_8$ and $R_9$ may represents a second group Z which is identical to or different from the first group Z;

$X^-$ represents a monovalent or divalent anion;
$R_{10}$ represents
a $C_1$–$C_6$ alkyl radical;
a monohydroxy($C_1$–$C_6$)alkyl radical;
a polyhydroxy($C_2$–$C_6$)alkyl radical;
an aryl radical;
a benzyl radical;
an amino($C_1$–$C_6$)alkyl radical,
an amino($C_1$–$C_6$)alkyl radical wherein the amine is protected with a ($C_1$–$C_6$)alkylcarbonyl, carbamyl or $C_1$–$C_6$ alkylsulphonyl radical;
a carboxy($C_1$–$C_6$)alkyl radical;
a cyano($C_1$–$C_6$)alkyl radical;
a carbamyl($C_1$–$C_6$)alkyl radical;
a trifluoro($C_1$–$C_6$)alkyl radical;
a tri($C_1$–$C_6$)alkylsilane($C_1$–$C_6$)alkyl radical,
a sulphonamido($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
a ($C_1$–$C_6$)alkylsulphonyl($C_1$–$C_6$)alkyl radical;
a ($C_1$–$C_6$)alkylketo($C_1$–$C_6$)alkyl radical;
an N-($C_1$–$C_6$)alkylcarbamyl($C_1$–$C_6$)alkyl radical;
an N-($C_1$–$C_6$)alkylsulphonamido($C_1$–$C_6$)alkyl radical;
x is an integer equal to 0 or 1; with the proviso that:
when x=0, then the divalent linker arm B is attached to the nitrogen atom bearing the radicals $R_7$ to $R_9$,
when x=1, then two of the radicals $R_7$ to $R_9$ form, together with the nitrogen atom to which they are attached, a saturated 5- or 6-membered ring as defined above, and the linker arm B is attached to a carbon atom of said saturated ring;

with the proviso that
the number of cationic groups Z in said compound or acid addition salt thereof is at least equal to 1;
when A represents a group —$NR_4R_5$, and when $R_4$ or $R_5$ represents a group Z, and when the divalent linker arm B represents an alkyl chain containing a ketone function, then said ketone function is not directly attached to the nitrogen atom of the group —$NR_4R_5$;

and further with the proviso that
4-amino-2-fluoro-N-(trimethylammonioethyl)aniline iodide;
4-amino-2-trifluoromethyl-N-(trimethylammonioethyl) aniline iodide;
4-amino-2-cyano-N-(trimethylammonioethyl)aniline iodide;
2-(4-aminophenylamino)ethyltrimethylammonium iodide;
4-amino-3-methyl-N-ethyl-N-(trimethylammonioethyl) aniline chloride;
compounds of formula (I) wherein $R_1$, $R_2$ and $R_3$ are each a hydrogen atom, x=0, A is a group —$NR_4R_5$ wherein one of said $R_4$ and $R_5$ is a hydrogen atom and the other of said $R_4$ and $R_5$ is a group Z wherein B is $C_1$–$C_6$ alkyl, one of said $R_7$, $R_8$ and $R_9$ is chosen from $C_1$–$C_4$ alkyl, monohydroxy ($C_1$–$C_4$)alkyl, and ($C_1$–$C_4$)alkoxy ($C_1$–$C_4$) alkyl groups; and the other two of said $R_7$, $R_8$ and $R_9$ are chosen from $C_1$–$C_6$ alkyl groups;
and acid addition salts thereof are excluded.

8. A method according to claim 7, wherein said keratin fibers are human keratin fibers.

9. A method according to claim 8, wherein said keratin fibers are hair.

10. A composition for the oxidation dyeing of keratin fibers comprising, in a medium suitable for dyeing, at least one oxidation base selected from the compounds of formula (1) and acid addition salts thereof:

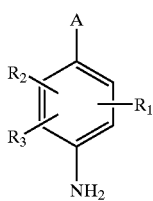

(1)

wherein:
$R_1$, $R_2$ and $R_3$, are identical or different and represent
a hydrogen atom;
a halogen atom;
a group Z;
a ($C_1$–$C_6$)alkylcarbonyl radical;
an amino($C_1$–$C_6$)alkylcarbonyl radical;
an N-Z-amino($C_1$–$C_6$)alkylcarbonyl radical;
an N-($C_1$–$C_6$)alkylamino($C_1$–$C_6$)alkylcarbonyl radical;
an N,N-di($C_1$–$C_6$)alkylamino($C_1$–$C_6$)alkylcarbonyl radical;
an amino($C_1$–$C_6$)alkylcarbonyl($C_1$–$C_6$)alkyl radical;
an N-Z-amino($C_1$–$C_6$)alkylcarbonyl($C_1$–$C_6$)alkyl radical;
an N-($C_1$–$C_6$)alkylamino($C_1$–$C_6$)alkylcarbonyl ($C_1$–$C_6$)alkyl radical;
an N,N-di($C_1$–$C_6$)alkylamino($C_1$–$C_6$)alkylcarbonyl ($C_1$–$C_6$)alkyl radical;
a carboxyl radical;
a ($C_1$–$C_6$)alkylcarboxyl radical;
a $C_1$–$C_6$ alkylsulphonyl radical;
an aminosulphonyl radical;
an N-Z-aminosulphonyl radical;
a $C_1$–$C_6$ N-alkylaminosulphonyl radical;
an N,N-di($C_1$–$C_6$)alkylaminosulphonyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a carbamyl radical;
an N-($C_1$–$C_6$)alkylcarbamyl radical;
an N,N-di($C_1$–$C_6$)alkylcarbamyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a $C_1$–$C_6$ alkyl radical;
a monohydroxy($C_1$–$C_6$)alkyl radical;
a polyhydroxy($C_2$–$C_6$)alkyl radical;
a ($C_1$–$C_6$)alkoxy($C_1$–$C_6$)alkyl radical;
a trifluoro($C_1$–$C_6$)alkyl radical;
a cyano radical;
a group $OR_6$;
a group $SR_6$;
an amino group protected with a ($C_1$–$C_6$)alkylcarbonyl, ($C_1$–$C_6$)alkylcarboxyl, trifluoro($C_1$–$C_6$)alkylcarbonyl, amino($C_1$–$C_6$)alkylcarbonyl, N-Z-amino($C_1$–$C_6$)alkylcarbonyl, N-($C_1$–$C_6$)alkylamino ($C_1$–$C_6$)alkylcarbonyl, N,N-di($C_1$–$C_6$)alkylamino ($C_1$–$C_6$)alkylcarbonyl, carbamyl, N-($C_1$–$C_6$) alkylcarbamyl, N,N-di($C_1$–$C_6$)alkylcarbamyl, $C_1$–$C_6$ alkylsulphonyl, aminosulphonyl, N-Z-aminosulphonyl, $C_1$–$C_6$ N-alkylaminosulphonyl, N,N-di($C_1$–$C_6$)alkylaminosulphonyl, thiocarbamyl or formyl radical, or with a group Z;
an amino($C_1$–$C_6$)alkyl radical wherein the amine is substituted with one or two identical or different radicals selected from $C_1$–$C_6$ alkyl, monohydroxy ($C_1$–$C_6$)alkyl, polyhydroxy($C_1$–$C_6$)alkyl, $C_1$–$C_6$ alkylcarbonyl, carbamyl, N-($C_1$–$C_6$)alkylcarbamyl, N,N-di($C_1$–$C_6$)alkylcarbamyl, ($C_1$–$C_6$) alkylsulphonyl, formyl, trifluoro($C_1$–$C_6$) alkylcarbonyl, ($C_1$–$C_6$)alkylcarboxyl and thiocarbamyl radicals, or with a group Z;

$R_6$ represents
a $C_1$–$C_6$ alkyl radical;
a monohydroxy($C_1$–$C_6$)alkyl radical;
a polyhydroxy($C_2$–$C_6$)alkyl radical;
a group Z;
a ($C_1$–$C_6$)alkoxy($C_1$–$C_6$)alkyl radical;
an aryl radical;
a benzyl radical;
a carboxy($C_1$–$C_6$)alkyl radical;
a ($C_1$–$C_6$)alkylcarboxy($C_1$–$C_6$)alkyl radical;
a cyano($C_1$–$C_6$)alkyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a trifluoro($C_1$–$C_6$)alkyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;

a (C$_1$–C$_6$)alkylsulphinyl(C$_1$–C$_6$)alkyl radical;
a (C$_1$–C$_6$)alkylsulphonyl(C$_1$–C$_6$)alkyl radical;
a (C$_1$–C$_6$)alkylcarbonyl(C$_1$–C$_6$)alkyl radical;
an amino(C$_1$–C$_6$)alkyl radical;
an amino(C$_1$–C$_6$)alkyl radical wherein the amine is substituted with one or two identical or different radicals selected from C$_1$–C$_6$ alkyl, monohydroxy(C$_1$–C$_6$)alkyl, polyhydroxy(C$_1$–C$_6$)alkyl, (C$_1$–C$_6$)alkylcarbonyl, formyl, trifluoro(C$_1$–C$_6$)alkylcarbonyl, (C$_1$–C$_6$)alkylcarboxyl, carbamyl, N-(C$_1$–C$_6$)alkylcarbamyl, N,N-di(C$_1$–C$_6$)alkylcarbamyl, thiocarbamyl and C$_1$–C$_6$ alkylsulphonyl radicals, and the group Z;

A represents a group —NR$_4$R$_5$ or a hydroxyl radical;

R$_4$ and R$_5$, are identical or different and represent
a hydrogen atom;
a group Z;
a C$_1$–C$_6$ alkyl radical;
a monohydroxy(C$_1$–C$_6$)alkyl radical;
a polyhydroxy(C$_2$–C$_6$)alkyl radical;
a (C$_1$–C$_6$)alkoxy(C$_1$–C$_6$)alkyl radical;
an aryl radical;
a benzyl radical;
a cyano(C$_1$–C$_6$)alkyl radical;
a carbamyl(C$_1$–C$_6$)alkyl radical;
an N-(C$_1$–C$_6$)alkylcarbamyl(C$_1$–C$_6$)alkyl radical;
an N,N-di(C$_1$–C$_6$)alkylcarbamyl(C$_1$–C$_6$)alkyl radical;
a thiocarbamyl(C$_1$–C$_6$)alkyl radical;
a trifluoro(C$_1$–C$_6$)alkyl radical;
a sulpho(C$_1$–C$_6$)alkyl radical;
a (C$_1$–C$_6$)alkylcarboxy(C$_1$–C$_6$)alkyl radical;
a (C$_1$–C$_6$)alkylsulphinyl(C$_1$–C$_6$)alkyl radical;
an aminosulphonyl(C$_1$–C$_6$)alkyl radical;
an N-Z-aminosulphonyl(C$_1$–C$_6$)alkyl radical;
an N-(C$_1$–C$_6$)alkylaminosulphonyl(C$_1$–C$_6$)alkyl radical;
an N,N-di(C$_1$–C$_6$)alkylaminosulphonyl(C$_1$–C$_6$)alkyl radical;
a (C$_1$–C$_6$)alkylcarbonyl(C$_1$–C$_6$)alkyl radical;
an amino(C$_1$–C$_6$)alkyl radical;
an amino(C$_1$–C$_6$)alkyl radical wherein the amine is substituted with one or two identical or different radicals selected from C$_1$–C$_6$ alkyl, monohydroxy(C$_1$–C$_6$)alkyl, polyhydroxy(C$_1$–C$_6$)alkyl, (C$_1$–C$_6$)alkylcarbonyl, carbamyl, N-(C$_1$–C$_6$)alkylcarbamyl, N,N-di(C$_1$–C$_6$)alkylcarbamyl, C$_1$–C$_6$ alkylsulphonyl, formyl, trifluoro(C$_1$–C$_6$)alkylcarbonyl, (C$_1$–C$_6$)alkylcarboxyl and thiocarbamyl radicals, or with a group Z;

Z represents a group of formula (II) below:

(II)

wherein:

B is a divalent linker arm which represents a linear or branched alkyl chain, said alkyl chain being uninterrupted or interrupted by one or more hetero atoms, and said alkyl chain being unsubstituted or substituted with one or more hydroxyl or C$_1$–C$_6$ alkoxy radicals, and which said chain has no ketone functions or at least one ketone function;

R$_7$, R$_8$ and R$_9$, are identical or different and represent
a C$_1$–C$_6$ alkyl radical,
a monohydroxy(C$_1$–C$_6$)alkyl radical,
a polyhydroxy(C$_2$–C$_6$)alkyl radical,
a (C$_1$–C$_6$)alkoxy(C$_1$–C$_6$)alkyl radical,
a cyano(C$_1$–C$_6$)alkyl radical,
an aryl radical,
a benzyl radical,
a carbamyl(C$_1$–C$_6$)alkyl radical,
a tri(C$_1$–C$_6$)alkylsilane(C$_1$–C$_6$)alkyl radical, or
an amino(C$_1$–C$_6$)alkyl radical wherein the amine is protected with a (C$_1$–C$_6$)alkylcarbonyl, carbamyl or C$_1$–C$_6$ alkylsulphonyl radical; or two of the radicals R$_7$, R$_8$ and R$_9$ together form, with the nitrogen atom to which they are attached, a saturated 5- or 6-membered carbon ring, wherein said ring may contain one or more additional hetero atoms, wherein said ring is unsubstituted or substituted with
a halogen atom,
a hydroxyl radical,
a C$_1$–C$_6$ alkyl radical,
a monohydroxy(C$_1$–C$_6$)alkyl radical,
a polyhydroxy(C$_2$–C$_6$)alkyl radical,
a nitro radical,
a cyano radical,
a cyano(C$_1$–C$_6$)alkyl radical,
a C$_1$–C$_6$ alkoxy radical,
a tri(C$_1$–C$_6$)alkylsilane(C$_1$–C$_6$)alkyl radical,
an amido radical,
an aldehydo radical,
a carboxyl radical,
a (C$_1$–C$_6$)alkylcarbonyl radical,
a thio radical,
a thio(C$_1$–C$_6$)alkyl radical,
a C$_1$–C$_6$ alkylthio radical,
an amino radical, or
an amino radical protected with a (C$_1$–C$_6$)alkylcarbonyl, carbamyl or C$_1$–C$_6$ alkylsulphonyl radical; and/or one of R$_7$, R$_8$ and R$_9$ may represents a second group Z which is identical to or different from the first group Z;

X$^-$ represents a monovalent or divalent anion;

R$_{10}$ represents
a C$_1$–C$_6$ alkyl radical;
a monohydroxy(C$_1$–C$_6$)alkyl radical;
a polyhydroxy(C$_2$–C$_6$)alkyl radical;
an aryl radical;
a benzyl radical;
an amino(C$_1$–C$_6$)alkyl radical,
an amino(C$_1$–C$_6$)alkyl radical wherein the amine is protected with a (C$_1$–C$_6$)alkylcarbonyl, carbamyl or C$_1$–C$_6$ alkylsulphonyl radical;
a carboxy(C$_1$–C$_6$)alkyl radical;
a cyano(C$_1$–C$_6$)alkyl radical;
a carbamyl(C$_1$–C$_6$)alkyl radical;
a trifluoro(C$_1$–C$_6$)alkyl radical;
a tri(C$_1$–C$_6$)alkylsilane(C$_1$–C$_6$)alkyl radical;
a sulphonamido(C$_1$–C$_6$)alkyl radical;
a (C$_1$–C$_6$)alkylcarboxy(C$_1$–C$_6$)alkyl radical;
a (C$_1$–C$_6$)alkylsulphinyl(C$_1$–C$_6$)alkyl radical;
a (C$_1$–C$_6$)alkylsulphonyl(C$_1$–C$_6$)alkyl radical;
a (C$_1$–C$_6$)alkylketo(C$_1$–C$_6$)alkyl radical;
an N-(C$_1$–C$_6$)alkylcarbamyl(C$_1$–C$_6$)alkyl radical;
an N-(C$_1$–C$_6$)alkylsulphonamido(C$_1$–C$_6$)alkyl radical;

x is an integer equal to 0 or 1; with the proviso that:
  when x=0, then the divalent linker arm B is attached to the nitrogen atom bearing the radicals $R_7$ to $R_9$,
  when x=1, then two of the radicals $R_7$ to $R_9$ form, together with the nitrogen atom to which they are attached, a saturated 5- or 6-membered ring as defined above, and the linker arm B is attached to a carbon atom of said saturated ring;
with the proviso that:
  the number of cationic groups Z in said compound or acid addition salt thereof is at least equal to 1;
  when A represents a group —$NR_4R_5$, and when $R_4$ or $R_5$ represents a group Z, and when the divalent linker arm B represents an alkyl chain containing a ketone function, then said ketone function is not directly attached to the nitrogen atom of the group —$NR_4R_5$;
and further with the proviso that
4-amino-2-fluoro-N-(trimethylammonioethyl)aniline iodide;
4-amino-2-trifluoromethyl-N-(trimethylammonioethyl) aniline iodide;
4-amino-2-cyano-N-(trimethylammonioethyl)aniline iodide;
2-(4-aminophenylamino)ethyltrimethylammonium iodide;
4-amino-3-methyl-N-ethyl-N-(trimethylammonioethyl) aniline chloride;
  compounds of formula (I) wherein A is a hydroxyl radical, two of said $R_1$, $R_2$ and $R_3$ are each a hydrogen atom, the other of said $R_1$, $R_2$ and $R_3$ is a group Z wherein x=0, B is —$CH_2$—, and one and only one of said $R_7$, $R_8$ and $R_9$ is chosen from 3-hydroxyphenyl radicals and 3-aminophenyl radicals;
  compounds of formula (I) wherein $R_1$, $R_2$ and $R_3$ are each a hydrogen atom, x=0, A is a group —$NR_4R_5$ wherein one of said $R_4$ and $R_5$ is a hydrogen atom and the other of said $R_4$ and $R_5$ is a group Z wherein B is $C_1$–$C_6$ alkyl, one of said $R_7$, $R_8$ and $R_9$ is chosen from $C_1$–$C_4$ alkyl, monohydroxy ($C_1$–$C_4$)alkyl, and ($C_1$–$C_4$)alkoxy ($C_1$–$C_4$)alkyl groups; and the other two of said $R_7$, $R_8$ and $R_9$ are chosen from $C_1$–$C_6$ alkyl groups;
and acid addition salts thereof are excluded.

11. A composition according to claim 10, wherein said keratin fibers are human keratin fibers.

12. A composition according to claim 11, wherein said human keratin fibers are hair.

13. A composition according to claim 10, wherein said at least one oxidation base is present in an amount ranging from 0.0005 to 12% by weight relative to the total weight of said composition.

14. A composition according to claim 13, wherein said at least one oxidation base is present in an amount ranging from 0.005 to 6% by weight relative to the total weight of said composition.

15. A composition according to claim 10, wherein said medium suitable for dyeing comprises water or a mixture of water and at least one organic solvent selected from C1–C4 lower alkanols, glycerol, glycols and glycol ethers, or aromatic alcohols.

16. A composition according to claim 15, wherein said at least one organic solvent is selected from ethanol, isopropanol, 2-butoxyethanol, propylene glycol, propylene glycol monomethyl ether, diethylene glycol monoethyl ether and monomethyl ether, benzyl alcohol, and phenoxyethanol.

17. A composition according to claim 10, having a pH ranging from about 3 to 12.

18. A composition according to claim 17, having a pH ranging from about 5 to about 11.

19. A composition according to claim 10, further comprising at least one additional oxidation base selected from para-phenylenediamines other than said at least one compound of formula (I), bis(phenyl)alkylenediamines, para-aminophenols other than said at least one compound of formula (I), ortho-aminophenols and heterocyclic bases.

20. A composition according to claim 19, wherein said at least one addtional oxidation base is selected from para-phenylenediamine, para-toluylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline, N,N'-bis(β-hydroxyethyl)-N,N'-bis(4-aminophenyl)-1,3-diaminopropanol, N,N'-bis(β13-hydroxyethyl)-N,N'-bis(4-aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine, N,N'-bis (ethyl)-N,N'-bis(4-amino-3-methylphenyl)ethylenediamine, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(-hydroxyethylaminomethyl)phenol, 2-aminophenol, 2-amino-5-methylphenol, 2-amino-6-methylphenol, 5-acetamido-2-aminophenol, pyridine derivatives, pyrimidine derivatives, and pyrazole derivatives.

21. A composition according to claim 19, wherein said at least one additional oxidation base is present in an amount ranging from 0.0005 to 12% by weight relative to the total weight of said composition.

22. A composition according to claim 21, wherein said at least one additional oxidation base is present in amount ranging from 0.005 to 6% by weight relative to the total weight of said composition.

23. A composition according to claim 10, further comprising at least one coupler and/or at least one direct dye.

24. A composition according to claim 23, wherein said at least one coupler is selected from meta-phenylenediamines, meta-aminophenols, meta-diphenols and heterocyclic couplers, and acid addition salts thereof.

25. A composition according to claim 24, wherein said at least one coupler is selected from indole derivatives, indolene derivatives, pyridine derivatives, pyrazolones, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 6-hydroxybenzomorpholine, 2,6-dihydroxy-4-methylpyridine, 1H-3-methylpyrazol-5-one, and 1-phenyl-3-methylpyrazol-5-one.

26. A composition according to claim 23, wherein said at least one coupler is present in an amount ranging from 0.0001 to 10% by weight relative to the total weight of said composition.

27. A composition according to claim 26, wherein said at least one coupler is present in an amount ranging from 0.005 to 5% by weight relative to the total weight of said composition.

28. A composition according to claim 10, wherein said acid addition salt is selected from hydrochlorides, hydrobromides, sulphates, citrates, succinates, tartrates, lactates and acetates.

29. A composition according to claim 10, wherein said composition is in the form of a liquid, a gel, or a cream.

30. A method for dyeing keratin fibers, comprising the steps of: applying a composition for the oxidation dyeing of keratin fibers comprising, in a medium suitable for dyeing, at least one oxidation base selected from the compounds of formula (1) and acid addition salts thereof:

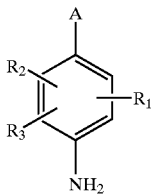

(1)

wherein:

$R_1$, $R_2$ and $R_3$, are identical or different and represent
  a hydrogen atom;
  a halogen atom;
  a group Z;
  a $(C_1-C_6)$alkylcarbonyl radical;
  an amino$(C_1-C_6)$alkylcarbonyl radical;
  an N-Z-amino$(C_1-C_6)$alkylcarbonyl radical;
  an N-$(C_1-C_6)$alkylamino$(C_1-C_6)$alkylcarbonyl radical;
  an N,N-di$(C_1-C_6)$alkylamino$(C_1-C_6)$alkylcarbonyl radical;
  an amino$(C_1-C_6)$alkylcarbonyl$(C_1-C_6)$alkyl radical;
  an N-Z-amino$(C_1-C_6)$alkylcarbonyl$(C_1-C_6)$alkyl radical;
  an N-$(C_1-C_6)$alkylamino$(C_1-C_6)$alkylcarbonyl $(C_1-C_6)$alkyl radical;
  an N,N-di$(C_1-C_6)$alkylamino$(C_1-C_6)$alkylcarbonyl $(C_1-C_6)$alkyl radical;
  a carboxyl radical;
  a $(C_1-C_6)$alkylcarboxyl radical;
  a $C_1-C_6$ alkylsulphonyl radical;
  an aminosulphonyl radical;
  an N-Z-aminosulphonyl radical;
  a $C_1-C_6$ N-alkylaminosulphonyl radical;
  an N,N-di$(C_1-C_6)$alkylaminosulphonyl radical;
  an aminosulphonyl$(C_1-C_6)$alkyl radical;
  an N-Z-aminosulphonyl$(C_1-C_6)$alkyl radical;
  an N-$(C_1-C_6)$alkylaminosulphonyl$(C_1-C_6)$alkyl radical;
  an N,N-di$(C_1-C_6)$alkylaminosulphonyl$(C_1-C_6)$alkyl radical;
  a carbamyl radical;
  an N-$(C_1-C_6)$alkylcarbamyl radical;
  an N,N-di$(C_1-C_6)$alkylcarbamyl radical;
  a carbamyl$(C_1-C_6)$alkyl radical;
  an N-$(C_1-C_6)$alkylcarbamyl$(C_1-C_6)$alkyl radical;
  an N,N-di$(C_1-C_6)$alkylcarbamyl$(C_1-C_6)$alkyl radical;
  a $C_1-C_6$ alkyl radical;
  a monohydroxy$(C_1-C_6)$alkyl radical;
  a polyhydroxy$(C_2-C_6)$alkyl radical;
  a $(C_1-C_6)$alkoxy$(C_1-C_6)$alkyl radical;
  a trifluoro$(C_1-C_6)$alkyl radical;
  a cyano radical;
  a group $OR_6$;
  a group $SR_6$;
  an amino group protected with a $(C_1-C_6)$alkylcarbonyl, $(C_1-C_6)$alkylcarboxyl, trifluoro$(C_1-C_6)$ alkylcarbonyl, amino$(C_1-C_6)$alkylcarbonyl, N-Z-amino$(C_1-C_6)$alkylcarbonyl, N-$(C_1-C_6)$alkylamino $(C_1-C_6)$alkylcarbonyl, N,N-di$(C_1-C_6)$alkylamino $(C_1-C_6)$alkylcarbonyl, carbamyl, N-$(C_1-C_6)$ alkylcarbamyl, N,N-di$(C_1-C_6)$alkylcarbamyl, $C_1-C_6$ alkylsulphonyl, aminosulphonyl, N-Z-aminosulphonyl, $C_1-C_6$ N-alkylaminosulphonyl, N,N-di$(C_1-C_6)$alkylaminosulphonyl, thiocarbamyl or formyl radical, or with a group Z;

an amino$(C_1-C_6)$alkyl radical wherein the amine is substituted with one or two identical or different radicals selected from $C_1-C_6$ alkyl, monohydroxy $(C_1-C_6)$alkyl, polyhydroxy$(C_1-C_6)$alkyl, $C_1-C_6$ alkylcarbonyl, carbamyl, N-$(C_1-C_6)$alkylcarbamyl, N,N-di$(C_1-C_6)$alkylcarbamyl, $(C_1-C_6)$ alkylsulphonyl, formyl, trifluoro$(C_1-C_6)$ alkylcarbonyl, $(C_1-C_6)$alkylcarboxyl and thiocarbamyl radicals, or with a group Z;

$R_6$ represents
  a $C_1-C_6$ alkyl radical;
  a monohydroxy$(C_1-C_6)$alkyl radical;
  a polyhydroxy$(C_2-C_6)$alkyl radical;
  a group Z;
  a $(C_1-C_6)$alkoxy$(C_1-C_6)$alkyl radical;
  an aryl radical;
  a benzyl radical;
  a carboxy$(C_1-C_6)$alkyl radical;
  a $(C_1-C_6)$alkylcarboxy$(C_1-C_6)$alkyl radical;
  a cyano$(C_1-C_6)$alkyl radical;
  a carbamyl$(C_1-C_6)$alkyl radical;
  an N-$(C_1-C_6)$alkylcarbamyl$(C_1-C_6)$alkyl radical;
  an N,N-di$(C_1-C_6)$alkylcarbamyl$(C_1-C_6)$alkyl radical;
  a trifluoro$(C_1-C_6)$alkyl radical;
  an aminosulphonyl$(C_1-C_6)$alkyl radical;
  an N-Z-aminosulphonyl$(C_1-C_6)$alkyl radical;
  an N-$(C_1-C_6)$alkylaminosulphonyl$(C_1-C_6)$alkyl radical;
  an N,N-di$(C_1-C_6)$alkylaminosulphonyl$(C_1-C_6)$alkyl radical;
  a $(C_1-C_6)$alkylsulphinyl$(C_1-C_6)$alkyl radical;
  a $(C_1-C_6)$alkylsulphonyl$(C_1-C_6)$alkyl radical;
  a $(C_1-C_6)$alkylcarbonyl$(C_1-C_6)$alkyl radical;
  an amino$(C_1-C_6)$alkyl radical;
  an amino$(C_1-C_6)$alkyl radical wherein the amine is substituted with one or two identical or different radicals selected from $C_1-C_6$ alkyl, monohydroxy $(C_1-C_6)$alkyl, polyhydroxy$(C_1-C_6)$alkyl, $(C_1-C_6)$ alkylcarbonyl, formyl, trifluoro$(C_1-C_6)$ alkylcarbonyl, $(C_1-C_6)$alkylcarboxyl, carbamyl, N-$(C_1-C_6)$alkylcarbamyl, N,N-di$(C_1-C_6)$ alkylcarbamyl, thiocarbamyl and $C_1-C_6$ alkylsulphonyl radicals, and the group Z;

A represents a group $-NR_4R_5$ or a hydroxyl radical;

$R_4$ and $R_5$, are identical or different and represent
  a hydrogen atom;
  a group Z;
  a $C_1-C_6$ alkyl radical;
  a monohydroxy$(C_1-C_6)$alkyl radical;
  a polyhydroxy$(C_2-C_6)$alkyl radical;
  a $(C_1-C_6)$alkoxy$(C_1-C_6)$alkyl radical;
  an aryl radical;
  a benzyl radical;
  a cyano$(C_1-C_6)$alkyl radical;
  a carbamyl$(C_1-C_6)$alkyl radical;
  an N-$(C_1-C_6)$alkylcarbamyl$(C_1-C_6)$alkyl radical;
  an N,N-di$(C_1-C_6)$alkylcarbamyl$(C_1-C_6)$alkyl radical;
  a thiocarbamyl$(C_1-C_6)$alkyl radical;

a trifluoro($C_1$–$C_6$)alkyl radical;
a sulpho($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a ($C_1$–$C_6$)alkylcarbonyl($C_1$–$C_6$)alkyl radical;
an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_1$–$C_6$)alkyl, ($C_1$–$C_6$)alkylcarbonyl, carbamyl, N-($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z;

Z represents a group of formula (II) below:

(II)

wherein:
B is a divalent linker arm which represents a linear or branched alkyl chain, said alkyl chain being uninterrupted or interrupted by one or more hetero atoms, and said alkyl chain being unsubstituted or substituted with one or more hydroxyl or $C_1$–$C_6$ alkoxy radicals, and which said chain has no ketone functions or at least one ketone function;

$R_7$, $R_8$ and $R_9$, are identical or different and represent
a $C_1$–$C_6$ alkyl radical,
a monohydroxy($C_1$–$C_6$)alkyl radical,
a polyhydroxy($C_2$–$C_6$)alkyl radical,
a ($C_1$–$C_6$)alkoxy($C_1$–$C_6$)alkyl radical,
a cyano($C_1$–$C_6$)alkyl radical,
an aryl radical,
a benzyl radical,
a carbamyl($C_1$–$C_6$)alkyl radical,
a tri($C_1$–$C_6$)alkylsilane($C_1$–$C_6$)alkyl radical, or
an amino($C_1$–$C_6$)alkyl radical wherein the amine is protected with a ($C_1$–$C_6$)alkylcarbonyl, carbamyl or $C_1$–$C_6$ alkylsulphonyl radical; or
two of the radicals $R_7$, $R_8$ and $R_9$ together form, with the nitrogen atom to which they are attached, a saturated 5- or 6-membered carbon ring, wherein said ring may contain one or more additional hetero atoms, wherein said ring is unsubstituted or substituted with
a halogen atom,
a hydroxyl radical,
a $C_1$–$C_6$ alkyl radical,
a monohydroxy($C_1$–$C_6$)alkyl radical,
a polyhydroxy($C_2$–$C_6$)alkyl radical,
a nitro radical,
a cyano radical,
a cyano($C_1$–$C_6$)alkyl radical,
a $C_1$–$C_6$ alkoxy radical,
a tri($C_1$–$C_6$)alkylsilane($C_1$–$C_6$)alkyl radical,
an amido radical,
an aldehydo radical,
a carboxyl radical,
a ($C_1$–$C_6$)alkylcarbonyl radical,
a thio radical,
a thio($C_1$–$C_6$)alkyl radical,
a $C_1$–$C_6$ alkylthio radical,
an amino radical, or
an amino radical protected with a ($C_1$–$C_6$)alkylcarbonyl, carbamyl or $C_1$–$C_6$ alkylsulphonyl radical; and/or
one of $R_7$, $R_8$ and $R_9$ may represents a second group Z which is identical to or different from the first group Z;

$X^-$ represents a monovalent or divalent anion;
$R_{10}$ represents
a $C_1$–$C_6$ alkyl radical;
a monohydroxy($C_1$–$C_6$)alkyl radical;
a polyhydroxy($C_2$–$C_6$)alkyl radical;
an aryl radical;
a benzyl radical;
an amino($C_1$–$C_6$)alkyl radical,
an amino($C_1$–$C_6$)alkyl radical wherein the amine is protected with a ($C_1$–$C_6$)alkylcarbonyl, carbamyl or $C_1$–$C_6$ alkylsulphonyl radical;
a carboxy($C_1$–$C_6$)alkyl radical;
a cyano($C_1$–$C_6$)alkyl radical;
a carbamyl($C_1$–$C_6$)alkyl radical;
a trifluoro($C_1$–$C_6$)alkyl radical;
a tri($C_1$–$C_6$)alkylsilane($C_1$–$C_6$)alkyl radical;
a sulphonamido($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
a ($C_1$–$C_6$)alkylsulphonyl($C_1$–$C_6$)alkyl radical;
a ($C_1$–$C_6$)alkylketo($C_1$–$C_6$)alkyl radical;
an N-($C_1$–$C_6$)alkylcarbamyl($C_1$–$C_6$)alkyl radical;
an N-($C_1$–$C_6$)alkylsulphonamido($C_1$–$C_6$)alkyl radical;
x is an integer equal to 0 or 1; with the proviso that:
when x=0, then the divalent linker arm B is attached to the nitrogen atom bearing the radicals $R_7$ to $R_9$,
when x=1, then two of the radicals $R_7$ to $R_9$ form, together with the nitrogen atom to which they are attached, a saturated 5- or 6-membered ring as defined above, and the linker arm B is attached to a carbon atom of said saturated ring;

with the proviso that:
the number of cationic groups Z in said compound or acid addition salt thereof is at least equal to 1;
when A represents a group —$NR_4R_5$, and when $R_4$ or $R_5$ represents a group Z, and when the divalent linker arm B represents an alkyl chain containing a ketone function, then said ketone function is not directly attached to the nitrogen atom of the group —$NR_4R_5$;
and further with the proviso that
4-amino-2-fluoro-N-(trimethylammonioethyl)aniline iodide;
4-amino-2-trifluoromethyl-N-(trimethylammonioethyl)aniline iodide;
4-amino-2-cyano-N-(trimethylammonioethyl)aniline iodide;
2-(4-aminophenylamino)ethyltrimethylammonium iodide;
4-amino-3-methyl-N-ethyl-N-(trimethylammonioethyl)aniline chloride;
compounds of formula (I) wherein A is a hydroxyl radical, two of said $R_1$, $R_2$ and $R_3$ are each a hydrogen atom, the other of said $R_1$, $R_2$ and $R_3$ is a group Z wherein x=0, B is —CH$_2$—, and one and only one of said R$_7$, R$_8$ and R$_9$ is chosen from 3-hydroxyphenyl radicals and 3-aminophenyl radicals;

compounds of formula (I) wherein R$_1$, R$_2$ and R$_3$ are each a hydrogen atom, x=0, A is a group —NR$_4$R$_5$ wherein one of said R$_4$ and R$_5$ is a hydrogen atom and the other of said R$_4$ and R$_5$ is a group Z wherein B is C$_1$–C$_6$ alkyl, one of said R$_7$, R$_8$ and R$_9$ is chosen from C$_1$–C$_4$ alkyl, monohydroxy (C$_1$–C$_4$)alkyl, and (C$_1$–C$_4$)alkoxy (C$_1$–C$_4$)alkyl groups; and the other two of said R$_7$, R$_8$ and R$_9$ are chosen from C$_1$–C$_6$ alkyl groups;

and acid addition salts thereof are excluded to said keratin fibers and developing color in acidic, neutral or alkaline pH using an oxidizing agent, wherein said oxidizing agent is either added to said oxidizing composition at the time of applying to said fibers, or is present in an oxidizing composition which is applied simultaneously or sequentially with said composition.

31. A method according to claim 30, wherein said oxidizing agent is selected from hydrogen peroxide, urea peroxide, alkali metal bromates and persalts.

32. A method according to claim 31, wherein said oxidizing agent is selected from perborates and persulphates.

33. A method according to claim 31, wherein said oxidizing agent is hydrogen peroxide.

34. A multi-component dyeing device or kit for dyeing keratin fibers comprising at least two compartments, wherein, a first compartment comprises a composition for the oxidation dyeing of keratin fibers comprising, in a medium suitable for dyeing, at least one oxidation base selected from the compounds of formula (1) and acid addition salts thereof:

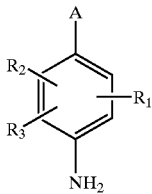

(1)

wherein:

R$_1$, R$_2$ and R$_3$, are identical or different and represent
a hydrogen atom;
a halogen atom;
a group Z;
a (C$_1$–C$_6$)alkylcarbonyl radical;
an amino(C$_1$–C$_6$)alkylcarbonyl radical;
an N-Z-amino(C$_1$–C$_6$)alkylcarbonyl radical;
an N-(C$_1$–C$_6$)alkylamino(C$_1$–C$_6$)alkylcarbonyl radical;
an N,N-di(C$_1$–C$_6$)alkylamino(C$_1$–C$_6$)alkylcarbonyl radical;
an amino(C$_1$–C$_6$)alkylcarbonyl(C$_1$–C$_6$)alkyl radical;
an N-Z-amino(C$_1$–C$_6$)alkylcarbonyl(C$_1$–C$_6$)alkyl radical;
an N-(C$_1$–C$_6$)alkylamino(C$_1$–C$_6$)alkylcarbonyl (C$_1$–C$_6$)alkyl radical;
an N,N-di(C$_1$–C$_6$)alkylamino(C$_1$–C$_6$)alkylcarbonyl (C$_1$–C$_6$)alkyl radical;
a carboxyl radical;
a (C$_1$–C$_6$)alkylcarboxyl radical;
a C$_1$–C$_6$ alkylsulphonyl radical;
an aminosulphonyl radical;
an N-Z-aminosulphonyl radical;
a C$_1$–C$_6$ N-alkylaminosulphonyl radical;
an N,N-di(C$_1$–C$_6$)alkylaminosulphonyl radical;
an aminosulphonyl(C$_1$–C$_6$)alkyl radical;
an N-Z-aminosulphonyl(C$_1$–C$_6$)alkyl radical;
an N-(C$_1$–C$_6$)alkylaminosulphonyl(C$_1$–C$_6$)alkyl radical;
an N,N-di(C$_1$–C$_6$)alkylaminosulphonyl(C$_1$–C$_6$)alkyl radical;
a carbamyl radical;
an N-(C$_1$–C$_6$)alkylcarbamyl radical;
an N,N-di(C$_1$–C$_6$)alkylcarbamyl radical;
a carbamyl(C$_1$–C$_6$)alkyl radical;
an N-(C$_1$–C$_6$)alkylcarbamyl(C$_1$–C$_6$)alkyl radical;
an N,N-di(C$_1$–C$_6$)alkylcarbamyl(C$_1$–C$_6$)alkyl radical;
a C$_1$–C$_6$ alkyl radical;
a monohydroxy(C$_1$–C$_6$)alkyl radical;
a polyhydroxy(C$_2$–C$_6$)alkyl radical;
a (C$_1$–C$_6$)alkoxy(C$_1$–C$_6$)alkyl radical;
a trifluoro(C$_1$–C$_6$)alkyl radical;
a cyano radical;
a group OR$_6$;
a group SR$_6$;
an amino group protected with a (C$_1$–C$_6$)alkylcarbonyl, (C$_1$–C$_6$)alkylcarboxyl, trifluoro(C$_1$–C$_6$)alkylcarbonyl, amino(C$_1$–C$_6$)alkylcarbonyl, N-Z-amino(C$_1$–C$_6$)alkylcarbonyl, N-(C$_1$–C$_6$)alkylamino(C$_1$–C$_6$)alkylcarbonyl, N,N-di(C$_1$–C$_6$)alkylamino(C$_1$–C$_6$)alkylcarbonyl, carbamyl, N-(C$_1$–C$_6$)alkylcarbamyl, N,N-di(C$_1$–C$_6$)alkylcarbamyl, C$_1$–C$_6$ alkylsulphonyl, aminosulphonyl, N-Z-aminosulphonyl, C$_1$–C$_6$ N-alkylaminosulphonyl, N,N-di(C$_1$–C$_6$)alkylaminosulphonyl, thiocarbamyl or formyl radical, or with a group Z;
an amino(C$_1$–C$_6$)alkyl radical wherein the amine is substituted with one or two identical or different radicals selected from C$_1$–C$_6$ alkyl, monohydroxy (C$_1$–C$_6$)alkyl, polyhydroxy(C$_1$–C$_6$)alkyl, C$_1$–C$_6$ alkylcarbonyl, carbamyl, N-(C$_1$–C$_6$)alkylcarbamyl, N,N-di(C$_1$–C$_6$)alkylcarbamyl, (C$_1$–C$_6$)alkylsulphonyl, formyl, trifluoro(C$_1$–C$_6$)alkylcarbonyl, (C$_1$–C$_6$)alkylcarboxyl and thiocarbamyl radicals, or with a group Z;

R$_6$ represents
a C$_1$–C$_6$ alkyl radical;
a monohydroxy(C$_1$–C$_6$)alkyl radical;
a polyhydroxy(C$_2$–C$_6$)alkyl radical;
a group Z;
a (C$_1$–C$_6$)alkoxy(C$_1$–C$_6$)alkyl radical;
an aryl radical;
a benzyl radical;
a carboxy(C$_1$–C$_6$)alkyl radical;
a (C$_1$–C$_6$)alkylcarboxy(C$_1$–C$_6$)alkyl radical;
a cyano(C$_1$–C$_6$)alkyl radical;
a carbamyl(C$_1$–C$_6$)alkyl radical;
an N-(C$_1$–C$_6$)alkylcarbamyl(C$_1$–C$_6$)alkyl radical;
an N,N-di(C$_1$–C$_6$)alkylcarbamyl(C$_1$–C$_6$)alkyl radical;
a trifluoro(C$_1$–C$_6$)alkyl radical;
an aminosulphonyl(C$_1$–C$_6$)alkyl radical;
an N-Z-aminosulphonyl(C$_1$–C$_6$)alkyl radical;
an N-(C$_1$–C$_6$)alkylaminosulphonyl(C$_1$–C$_6$)alkyl radical;
an N,N-di(C$_1$–C$_6$)alkylaminosulphonyl(C$_1$–C$_6$)alkyl radical;
a (C$_1$–C$_6$)alkylsulphinyl(C$_1$–C$_6$)alkyl radical;
a (C$_1$–C$_6$)alkylsulphonyl(C$_1$–C$_6$)alkyl radical;
a (C$_1$–C$_6$)alkylcarbonyl(C$_1$–C$_6$)alkyl radical;
an amino(C$_1$–C$_6$)alkyl radical;

an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_1$–$C_6$)alkyl, ($C_1$–$C_6$) alkylcarbonyl, formyl, trifluoro($C_1$–$C_6$) alkylcarbonyl, ($C_1$–$C_6$)alkylcarboxyl, carbamyl, N-($C_1$–$C_6$)alkylcarbamyl, N,N-di($C_1$–$C_6$) alkylcarbamyl, thiocarbamyl and $C_1$–$C_6$ alkylsulphonyl radicals, and the group Z;

A represents a group —$NR_4R_5$ or a hydroxyl radical;

$R_4$ and $R_5$, are identical or different and represent
a hydrogen atom;
a group Z;
a $C_1$–$C_6$ alkyl radical;
a monohydroxy($C_1$–$C_6$)alkyl radical;
a polyhydroxy($C_2$–$C_6$)alkyl radical;
a ($C_1$–$C_6$)alkoxy($C_1$–$C_6$)alkyl radical;
an aryl radical;
a benzyl radical;
a cyano($C_1$–$C_6$)alkyl radical;
a carbamyl($C_1$–$C_6$)alkyl radical;
an N-($C_1$–$C_6$)alkylcarbamyl($C_1$–$C_6$)alkyl radical;
an N,N-di($C_1$–$C_6$)alkylcarbamyl($C_1$–$C_6$)alkyl radical;
a thiocarbamyl($C_1$–$C_6$)alkyl radical;
a trifluoro($C_1$–$C_6$)alkyl radical;
a sulpho($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
an aminosulphonyl($C_1$–$C_6$)alkyl radical;
an N-Z-aminosulphonyl($C_1$–$C_6$)alkyl radical;
an N-($C_1$–$C_6$)alkylaminosulphonyl($C_1$–$C_6$)alkyl radical;
an N,N-di($C_1$–$C_6$)alkylaminosulphonyl($C_1$–$C_6$)alkyl radical;
a ($C_1$–$C_6$)alkylcarbonyl($C_1$–$C_6$)alkyl radical;
an amino($C_1$–$C_6$)alkyl radical;
an amino($C_1$–$C_6$)alkyl radical wherein the amine is substituted with one or two identical or different radicals selected from $C_1$–$C_6$ alkyl, monohydroxy($C_1$–$C_6$)alkyl, polyhydroxy($C_1$–$C_6$)alkyl, ($C_1$–$C_6$) alkylcarbonyl, carbamyl, N-($C_1$–$C_6$)alkylcarbamyl, N,N-di($C_1$–$C_6$)alkylcarbamyl, $C_1$–$C_6$ alkylsulphonyl, formyl, trifluoro($C_1$–$C_6$) alkylcarbonyl, ($C_1$–$C_6$)alkylcarboxyl and thiocarbamyl radicals, or with a group Z;

Z represents a group of formula (II) below:

(II)

wherein:
B is a divalent linker arm which represents a linear or branched alkyl chain, said alkyl chain being uninterrupted or interrupted by one or more hetero atoms, and said alkyl chain being unsubstituted or substituted with one or more hydroxyl or $C_1$–$C_6$ alkoxy radicals, and which said chain has no ketone functions or at least one ketone function;

$R_7$, $R_8$ and $R_9$, are identical or different and represent
a $C_1$–$C_6$ alkyl radical,
a monohydroxy($C_1$–$C_6$)alkyl radical,
a polyhydroxy($C_2$–$C_6$)alkyl radical,
a ($C_1$–$C_6$)alkoxy($C_1$–$C_6$)alkyl radical,
a cyano($C_1$–$C_6$)alkyl radical,
an aryl radical,
a benzyl radical,
a carbamyl($C_1$–$C_6$)alkyl radical,
a tri($C_1$–$C_6$)alkylsilane($C_1$–$C_6$)alkyl radical, or
an amino($C_1$–$C_6$)alkyl radical wherein the amine is protected with a ($C_1$–$C_6$)alkylcarbonyl, carbamyl or $C_1$–$C_6$ alkylsulphonyl radical; or
two of the radicals $R_7$, $R_8$ and $R_9$ together form, with the nitrogen atom to which they are attached, a saturated 5- or 6-membered carbon ring, wherein said ring may contain one or more additional hetero atoms, wherein said ring is unsubstituted or substituted with
a halogen atom,
a hydroxyl radical,
a $C_1$–$C_6$ alkyl radical,
a monohydroxy($C_1$–$C_6$)alkyl radical,
a polyhydroxy($C_2$–$C_6$)alkyl radical,
a nitro radical,
a cyano radical,
a cyano($C_1$–$C_6$)alkyl radical,
a $C_1$–$C_6$ alkoxy radical,
a tri($C_1$–$C_6$)alkylsilane($C_1$–$C_6$)alkyl radical,
an amido radical,
an aldehydo radical,
a carboxyl radical,
a ($C_1$–$C_6$)alkylcarbonyl radical,
a thio radical,
a thio($C_1$–$C_6$)alkyl radical,
a $C_1$–$C_6$ alkylthio radical,
an amino radical, or
an amino radical protected with a ($C_1$–$C_6$) alkylcarbonyl, carbamyl or $C_1$–$C_6$ alkylsulphonyl radical; and/or
one of $R_7$, $R_8$ and $R_9$ may represents a second group Z which is identical to or different from the first group Z;

$X^-$ represents a monovalent or divalent anion;

$R_{10}$ represents
a $C_1$–$C_6$ alkyl radical;
a monohydroxy($C_1$–$C_6$)alkyl radical;
a polyhydroxy($C_2$–$C_6$)alkyl radical;
an aryl radical;
a benzyl radical;
an amino($C_1$–$C_6$)alkyl radical,
an amino($C_1$–$C_6$)alkyl radical wherein the amine is protected with a ($C_1$–$C_6$)alkylcarbonyl, carbamyl or $C_1$–$C_6$ alkylsulphonyl radical;
a carboxy($C_1$–$C_6$)alkyl radical;
a cyano($C_1$–$C_6$)alkyl radical;
a carbamyl($C_1$–$C_6$)alkyl radical;
a trifluoro($C_1$–$C_6$)alkyl radical;
a tri($C_1$–$C_6$)alkylsilane($C_1$–$C_6$)alkyl radical;
a sulphonamido($C_1$–$C_6$)alkyl radical;
a ($C_1$–$C_6$)alkylcarboxy($C_1$–$C_6$)alkyl radical;
a ($C_1$–$C_6$)alkylsulphinyl($C_1$–$C_6$)alkyl radical;
a ($C_1$–$C_6$)alkylsulphonyl($C_1$–$C_6$)alkyl radical;
a ($C_1$–$C_6$)alkylketo($C_1$–$C_6$)alkyl radical;
an N-($C_1$–$C_6$)alkylcarbamyl($C_1$–$C_6$)alkyl radical;
an N-($C_1$–$C_6$)alkylsulphonamido($C_1$–$C_6$)alkyl radical;

x is an integer equal to 0 or 1; with the proviso that:
when x=0, then the divalent linker arm B is attached to the nitrogen atom bearing the radicals $R_7$ to $R_9$,
when x=1, then two of the radicals $R_7$ to $R_9$ form, together with the nitrogen atom to which they are attached, a saturated 5- or 6-membered ring as defined above, and the linker arm B is attached to a carbon atom of said saturated ring;

with the proviso that:
the number of cationic groups Z in said compound or acid addition salt thereof is at least equal to 1;
when A represents a group —NR$_4$R$_5$, and when R$_4$ or R$_5$ represents a group Z, and when the divalent linker arm B represents an alkyl chain containing a ketone function, then said ketone function is not directly attached to the nitrogen atom of the group —NR$_4$R$_5$;

and further with the proviso that
4-amino-2-fluoro-N-(trimethylammonioethyl)aniline iodide;
4-amino-2-trifluoromethyl-N-(trimethylammonioethyl) aniline iodide;
4-amino-2-cyano-N-(trimethylammonioethyl)aniline iodide;
2-(4-aminophenylamino)ethyltrimethylammonium iodide;
4-amino-3-methyl-N-ethyl-N-(trimethylammonioethyl) aniline chloride;

compounds of formula (I) wherein A is a hydroxyl radical, two of said R$_1$, R$_2$ and R$_3$ are each a hydrogen atom, the other of said R$_1$, R$_2$ and R$_3$ is a group Z wherein x=0, B is —CH$_2$—, and one and only one of said R$_7$, R$_8$ and R$_9$ is chosen from 3-hydroxyphenyl radicals and 3-aminophenyl radicals;

compounds of formula (I) wherein R$_1$, R$_2$ and R$_3$ are each a hydrogen atom, x=0, A is a group —NR$_4$R$_5$ wherein one of said R$_4$ and R$_5$ is a hydrogen atom and the other of said R$_4$ and R$_5$ is a group Z wherein B is C$_1$–C$_6$ alkyl, one of said R$_7$, R$_8$ and R$_9$ is chosen from C$_1$–C$_4$ alkyl, monohydroxy (C$_1$–C$_4$)alkyl, and (C$_1$–C$_4$)alkoxy (C$_1$–C$_4$)alkyl groups; and the other two of said R$_7$, R$_8$ and R$_9$ are chosen from C$_1$–C$_6$ alkyl groups;

and acid addition salts thereof are excluded and
a second compartment comprises an oxidizing composition.

* * * * *

UNITED STATES PATENT AND TRADEMARK OFFICE
CERTIFICATE OF CORRECTION

PATENT NO.   : 6,565,614 B1
DATED        : May 20, 2003
INVENTOR(S)  : Alain Genet and Alain LaGrange It is certified that error appears in the above-identified patent and that said Letters Patent is hereby corrected as shown below:

Title page,
Item [75], Inventors, "Aulay-sous-Bois" should read -- Aulnay-sous-Bois --; and "Alain LaGrange" should read -- Alain Lagrange --.
Item [57], ABSTRACT,
Line 5, "then" should read -- them --.

Column 21,
Line 9, "alkylsulfonoyl" should read -- alkylsulphonyl --.
Line 10, "aminosulfonyl" should read -- aminosulphonyl --.
Line 11, "N-Z-aminosulfonyl" should read -- N-Z-aminosulphonyl --.

Column 27,
Line 12, "$R_4$and" should read -- $R_4$ and --.
Line 66, "polyhydroxy($C_2C_6$)alkyl" should read -- polyhydroxy($C_2$-$C_6$)alkyl --.

Column 28,
Line 8, "$C_1$-$C_6$alkylsulphonyl" should read -- $C_1$-$C_6$ alkylsulphony --.
Line 19, "polyhydroxy($C_1$-$C_6$)alkyl" should read -- polyhydroxy($C_2$-$C_6$)alkyl --.
Line 35, "and/or," should read -- and/or --.

Column 29,
Line 3, "proviso that" should read -- proviso that: --.

Column 34,
Lines 16-17, "N,N'-bis($\beta$13-hydroxyethyl)-N,N'-bis(4-aminophenyl)ethylenediamine," should read -- N,N'-bis($\beta$-hydroxyethyl)-N,N'-bis(4-aminophenyl)ethylenediamine, --.

Signed and Sealed this

Eighth Day of July, 2003

JAMES E. ROGAN
*Director of the United States Patent and Trademark Office*